United States Patent
Boyajian et al.

(10) Patent No.: US 12,290,700 B2
(45) Date of Patent: May 6, 2025

(54) ADJUSTABLE ILLUMINATOR FOR PHOTODYNAMIC THERAPY AND DIAGNOSIS

(71) Applicant: Sun Pharmaceutical Industries, Inc., Princeton, NJ (US)

(72) Inventors: Thomas Boyajian, Wilmington, MA (US); Mark Carota, Chelmsford, MA (US); Brian Mazejka, Salem, NH (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 234 days.

(21) Appl. No.: 17/889,115

(22) Filed: Aug. 16, 2022

(65) Prior Publication Data

US 2022/0387816 A1 Dec. 8, 2022

Related U.S. Application Data

(60) Continuation of application No. 16/791,004, filed on Feb. 14, 2020, now Pat. No. 11,446,512, which is a
(Continued)

(51) Int. Cl.
*A61N 5/06* (2006.01)
*A61B 5/00* (2006.01)

(52) U.S. Cl.
CPC ............ *A61N 5/062* (2013.01); *A61B 5/0064* (2013.01); *A61B 5/0082* (2013.01);
(Continued)

(58) Field of Classification Search
CPC ........ A61N 5/06; A61N 5/062; A61N 5/0616; A61N 2005/0626; A61N 2005/0652;
(Continued)

(56) References Cited

U.S. PATENT DOCUMENTS

| 4,100,415 A | 7/1978 | Blaisdell et al. |
| 4,344,256 A | 8/1982 | King |

(Continued)

FOREIGN PATENT DOCUMENTS

| AU | 43869/01 A1 | 5/2001 |
| BR | 102014019194-1 B1 | 10/2022 |

(Continued)

OTHER PUBLICATIONS

A Pharmacokinetic Study of Levulan Kerastick (aminolevulinic acid HCl) for Topical Solution, 20%, Under Maximal Use Conditions, Clinical Study Report, DUSA Pharmaceuticals, Jun. 10, 2015, 68 pages.
(Continued)

*Primary Examiner* — Tammie K Marlen
(74) *Attorney, Agent, or Firm* — Foley & Lardner LLP

(57) ABSTRACT

An adjustable illuminator for photodynamically diagnosing or treating a surface includes a plurality of first panels and at least one second panel. The plurality of first panels have wider widths and the at least one second panel has a narrower width. The narrower width is less than the wider widths. The illuminator further includes a plurality of light sources, each mounted to one of the plurality of first panels or the at least one second panel and configured to irradiate the surface with substantially uniform intensity visible light. The plurality of first panels and the at least one second panel are rotatably connected. The at least one second panel is connected on each side to one of the plurality of first panels. The second panel acts as a "lighted hinge" to reduce or eliminate optical dead spaces between adjacent panels when the illuminator is bent into a certain configuration.

15 Claims, 8 Drawing Sheets

Related U.S. Application Data division of application No. 15/292,731, filed on Oct. 13, 2016, now Pat. No. 10,589,122.

(60) Provisional application No. 62/241,902, filed on Oct. 15, 2015.

(52) U.S. Cl.
CPC ............... *A61N 2005/0626* (2013.01); *A61N 2005/0633* (2013.01); *A61N 2005/0642* (2013.01); *A61N 2005/0651* (2013.01); *A61N 2005/0652* (2013.01); *A61N 2005/0662* (2013.01); *A61N 2005/0663* (2013.01)

(58) Field of Classification Search
CPC .... A61N 2005/0633; A61N 2005/0642; A61N 2005/0663; A61N 2005/0636; A61N 2005/064; A61N 2005/0658; A61N 2005/0651; A61N 2005/0662; A61B 5/0064; A61B 5/0082

See application file for complete search history.

(56) References Cited

U.S. PATENT DOCUMENTS

| | | |
|---|---|---|
| 4,667,658 A | 5/1987 | Guibert |
| 4,805,202 A | 2/1989 | Deucher et al. |
| 4,823,858 A | 4/1989 | Perutz |
| 4,832,294 A | 5/1989 | Eidem |
| 5,032,400 A | 7/1991 | Wiersum et al. |
| 5,079,262 A | 1/1992 | Kennedy et al. |
| 5,211,938 A | 5/1993 | Kennedy et al. |
| 5,441,531 A | 8/1995 | Zarate et al. |
| 5,474,528 A | 12/1995 | Meserol |
| 5,489,279 A | 2/1996 | Meserol |
| 5,505,726 A | 4/1996 | Meserol |
| 5,601,838 A | 2/1997 | Hind |
| 5,686,065 A | 11/1997 | Haney |
| 5,782,895 A | 7/1998 | Zarate et al. |
| 5,814,008 A | 9/1998 | Chen et al. |
| 5,849,027 A | 12/1998 | Gart et al. |
| 5,954,703 A | 9/1999 | Golub |
| 6,223,071 B1 | 4/2001 | Lundahl et al. |
| 6,231,593 B1 | 5/2001 | Meserol |
| 6,290,713 B1 | 9/2001 | Russell |
| 6,559,183 B1 | 5/2003 | Schmid et al. |
| 6,709,446 B2 | 3/2004 | Lundahl et al. |
| 6,897,238 B2 | 5/2005 | Anderson |
| 6,979,101 B2 | 12/2005 | Sauska et al. |
| 7,001,413 B2 | 2/2006 | Butler |
| 7,033,381 B1 | 4/2006 | Larsen |
| 7,131,990 B2 | 11/2006 | Bansal et al. |
| 7,156,865 B2 | 1/2007 | Waldmann |
| 7,190,109 B2 | 3/2007 | Lundahl et al. |
| 7,311,722 B2 | 12/2007 | Larsen |
| 7,347,573 B1 | 3/2008 | Isler |
| 7,723,910 B2 | 5/2010 | Lundahl et al. |
| 7,730,893 B2 | 6/2010 | Dougal |
| 8,030,836 B2 | 10/2011 | Lundahl et al. |
| 8,216,289 B2 | 7/2012 | Lundahl et al. |
| 8,226,289 B2 | 7/2012 | Lindeberg |
| 8,451,601 B2 | 5/2013 | Bohn et al. |
| 8,608,737 B2 | 12/2013 | Mehta et al. |
| 8,638,546 B2 | 1/2014 | Hoshino |
| 8,758,418 B2 | 6/2014 | Lundahl et al. |
| 8,759,396 B2 | 6/2014 | Wulf et al. |
| 8,899,791 B2 | 12/2014 | Liu |
| 8,947,320 B2 | 2/2015 | King et al. |
| 9,009,984 B2 | 4/2015 | Caskey et al. |
| 9,108,045 B2 | 8/2015 | Sakamoto et al. |
| 9,227,082 B2 * | 1/2016 | McDaniel ............ A61B 18/203 |
| 9,492,681 B2 | 11/2016 | Aydt et al. |
| 9,533,170 B2 | 1/2017 | Dye et al. |
| 9,597,150 B2 | 3/2017 | Lundahl |
| 9,723,991 B2 | 8/2017 | Lundahl et al. |
| 10,029,116 B2 | 7/2018 | Lundahl |
| 10,357,567 B1 | 7/2019 | Lundahl et al. |
| 10,589,122 B2 | 3/2020 | Boyajian et al. |
| 10,603,508 B2 | 3/2020 | Boyajian et al. |
| 10,688,147 B2 | 6/2020 | Garruto et al. |
| 10,786,571 B2 | 9/2020 | Solioz et al. |
| 10,814,114 B2 | 10/2020 | Boyajian et al. |
| 11,135,293 B2 | 10/2021 | Lundahl et al. |
| 11,179,574 B2 | 11/2021 | Boyajian et al. |
| 11,235,169 B1 | 2/2022 | Osterloh et al. |
| 11,333,336 B1 | 5/2022 | Tobin et al. |
| 11,446,512 B2 | 9/2022 | Boyajian et al. |
| 11,571,478 B2 | 2/2023 | Lundahl et al. |
| 11,697,028 B2 | 7/2023 | Boyajian et al. |
| 2001/0021812 A1* | 9/2001 | Lundahl ................ A61N 5/062 600/476 |
| 2002/0029071 A1 | 3/2002 | Whitehurst |
| 2003/0088296 A1 | 5/2003 | Waldmann |
| 2003/0216795 A1 | 11/2003 | Harth et al. |
| 2004/0010299 A1 | 1/2004 | Tolkoff et al. |
| 2004/0068305 A1* | 4/2004 | Bansal ................. A61N 5/0621 607/89 |
| 2004/0093043 A1 | 5/2004 | Edel et al. |
| 2004/0143308 A1 | 7/2004 | Lundahl et al. |
| 2004/0162596 A1 | 8/2004 | Altshuler et al. |
| 2004/0260365 A1 | 12/2004 | Groseth et al. |
| 2005/0075703 A1 | 4/2005 | Larsen |
| 2005/0090877 A1 | 4/2005 | Harth et al. |
| 2005/0093485 A1 | 5/2005 | Spivak |
| 2005/0157499 A1 | 7/2005 | Kim |
| 2006/0182790 A1 | 8/2006 | Mayoral |
| 2006/0241726 A1 | 10/2006 | Whitehurst |
| 2006/0253175 A1 | 11/2006 | Fan et al. |
| 2006/0274549 A1 | 12/2006 | Fukuyoshi |
| 2006/0287696 A1 | 12/2006 | Wright et al. |
| 2007/0021806 A1 | 1/2007 | Mercier et al. |
| 2007/0088410 A1 | 4/2007 | Chung et al. |
| 2007/0283655 A1 | 12/2007 | Tobin |
| 2008/0031924 A1 | 2/2008 | Gilson et al. |
| 2008/0180950 A1 | 7/2008 | Kang et al. |
| 2008/0188558 A1 | 8/2008 | Godal et al. |
| 2009/0099499 A1 | 4/2009 | Persin et al. |
| 2009/0177190 A1 | 7/2009 | Lee |
| 2009/0247932 A1 | 10/2009 | Barolet |
| 2009/0270946 A1 | 10/2009 | Spivak |
| 2009/0324727 A1 | 12/2009 | Foguet Roca |
| 2010/0010591 A1 | 1/2010 | Daffer |
| 2010/0118522 A1 | 5/2010 | Hente |
| 2010/0174222 A1 | 7/2010 | Mcdaniel |
| 2010/0174223 A1 | 7/2010 | Sakamoto et al. |
| 2010/0179469 A1 | 7/2010 | Hammond et al. |
| 2010/0298758 A1 | 11/2010 | Christiansen et al. |
| 2011/0020441 A1 | 1/2011 | Klaveness et al. |
| 2011/0053965 A1 | 3/2011 | Trigiante |
| 2011/0106222 A1 | 5/2011 | Wilson et al. |
| 2011/0218597 A1 | 9/2011 | Wang |
| 2011/0224598 A1 | 9/2011 | Barolet |
| 2011/0243789 A1 | 10/2011 | Roberts |
| 2011/0270092 A1 | 11/2011 | Kang et al. |
| 2011/0293528 A1 | 12/2011 | Godal et al. |
| 2012/0004711 A1 | 1/2012 | Hilty |
| 2012/0035719 A1 | 2/2012 | Forster et al. |
| 2012/0104277 A1 | 5/2012 | Morren |
| 2012/0129879 A1 | 5/2012 | Cantrell et al. |
| 2012/0283328 A1 | 11/2012 | Modi |
| 2012/0287671 A1 | 11/2012 | Parker et al. |
| 2012/0296260 A1 | 11/2012 | Vizethum et al. |
| 2012/0303101 A1 | 11/2012 | Rogers et al. |
| 2013/0066404 A1 | 3/2013 | Tapper et al. |
| 2013/0066405 A1 | 3/2013 | Dougal |
| 2013/0102906 A1 | 4/2013 | Lundahl et al. |
| 2013/0190845 A1 | 7/2013 | Liu et al. |
| 2013/0274834 A1 | 10/2013 | Barolet et al. |
| 2013/0289089 A1 | 10/2013 | Morris et al. |
| 2013/0304019 A1 | 11/2013 | Cooper et al. |
| 2013/0315999 A1 | 11/2013 | Paithankar et al. |
| 2014/0010761 A1 | 1/2014 | Parent et al. |
| 2014/0067024 A1 | 3/2014 | Jones et al. |

(56) References Cited

U.S. PATENT DOCUMENTS

| | | |
|---|---|---|
| 2014/0121631 A1 | 5/2014 | Bean et al. |
| 2014/0303547 A1 | 10/2014 | Loupis et al. |
| 2015/0018751 A1 | 1/2015 | Kerber |
| 2015/0021221 A1 | 1/2015 | Hendrickson et al. |
| 2015/0162109 A1 | 6/2015 | Nager |
| 2015/0190651 A1 | 7/2015 | Jayavanth et al. |
| 2015/0217132 A1 | 8/2015 | Makkapati et al. |
| 2015/0238776 A1 | 8/2015 | Sakamoto et al. |
| 2015/0290028 A1 | 10/2015 | Isserow et al. |
| 2015/0290470 A1 | 10/2015 | Tapper et al. |
| 2016/0008623 A1 | 1/2016 | Jones et al. |
| 2016/0030565 A1 | 2/2016 | Wulf et al. |
| 2016/0045015 A1 | 2/2016 | Baldwin |
| 2016/0045757 A1 | 2/2016 | Groseth |
| 2016/0051832 A1 | 2/2016 | Mordon |
| 2016/0166846 A1 | 6/2016 | Chae |
| 2016/0175608 A1 | 6/2016 | Livingston |
| 2016/0175609 A1 | 6/2016 | Dye et al. |
| 2016/0175610 A1 | 6/2016 | Livingston et al. |
| 2016/0255941 A1 | 9/2016 | Yang et al. |
| 2016/0346392 A1 | 12/2016 | Wulf |
| 2017/0106205 A1 | 4/2017 | Boyajian et al. |
| 2017/0216616 A1 | 8/2017 | Boyajian et al. |
| 2018/0043178 A1 | 2/2018 | Iguchi et al. |
| 2018/0178034 A1 | 6/2018 | Iguchi et al. |
| 2018/0311507 A1 | 11/2018 | Barolet |
| 2018/0344852 A1 | 12/2018 | Solioz et al. |
| 2019/0105261 A1 | 4/2019 | Waugh et al. |
| 2019/0216927 A1 | 7/2019 | Lundahl et al. |
| 2019/0290763 A1 | 9/2019 | Lundahl et al. |
| 2020/0100997 A1 | 4/2020 | Soler et al. |
| 2020/0261580 A1 | 8/2020 | Willey |
| 2020/0269063 A1 | 8/2020 | Boyajian et al. |
| 2020/0398071 A1 | 12/2020 | Boyajian et al. |
| 2022/0008538 A1 | 1/2022 | Lundahl et al. |
| 2022/0040494 A1 | 2/2022 | Boyajian et al. |
| 2022/0370610 A1 | 11/2022 | Lundahl et al. |
| 2022/0387816 A1 | 12/2022 | Boyajian et al. |
| 2023/0001227 A1 | 1/2023 | Boyajian et al. |
| 2023/0131170 A1 | 4/2023 | Sanghvi et al. |
| 2024/0335360 A1 | 10/2024 | Foguet et al. |
| 2024/0335380 A1 | 10/2024 | Foguet et al. |

FOREIGN PATENT DOCUMENTS

| | | |
|---|---|---|
| CA | 2706642 C | 8/2002 |
| CA | 2568744 A1 | 12/2005 |
| CA | 2738861 A1 | 7/2011 |
| CN | 1941799 A | 4/2007 |
| CN | 103043330 A | 4/2013 |
| CN | 203097540 U | 7/2013 |
| CN | 206822964 U | 1/2018 |
| DE | 69827286 T2 | 11/2005 |
| EP | 1 162 400 A2 | 12/2001 |
| EP | 1 238 652 A1 | 9/2002 |
| EP | 1 311 259 B1 | 5/2003 |
| EP | 2 456 382 B1 | 5/2012 |
| EP | 3 143 986 A1 | 3/2017 |
| FR | 2813747 A | 3/2002 |
| JP | S49-002185 | 1/1974 |
| JP | H04-500770 A | 2/1992 |
| JP | 2524147 B2 | 8/1996 |
| JP | 2731032 B | 3/1998 |
| JP | 2736475 B2 | 4/1998 |
| JP | H11-239624 A | 9/1999 |
| JP | 2000-177155 A | 6/2000 |
| JP | 2002-529495 A | 9/2002 |
| JP | 2006-511275 A | 4/2006 |
| JP | 2006-519047 A | 8/2006 |
| JP | 2009-055969 A | 3/2009 |
| JP | 2010-513363 | 4/2010 |
| JP | 2010-515714 A | 5/2010 |
| JP | 2010-212819 A | 9/2010 |
| JP | 4855775 B2 | 1/2012 |
| JP | 2013-019237 A | 1/2013 |
| JP | 2014-067529 A | 4/2014 |
| KR | 20070063718 A | 6/2007 |
| KR | 20090005028 A | 1/2009 |
| KR | 20090055891 A | 6/2009 |
| KR | 101180416 B1 | 9/2012 |
| KR | 20120100861 A | 9/2012 |
| KR | 101237952 B1 | 2/2013 |
| KR | 101244434 B1 | 3/2013 |
| KR | 101576623 B1 | 12/2015 |
| WO | WO-87/07321 A1 | 12/1987 |
| WO | WO-93/09847 A1 | 5/1993 |
| WO | WO-95/07077 A1 | 9/1993 |
| WO | WO-96/06602 A1 | 3/1996 |
| WO | WO-97/15226 A1 | 5/1997 |
| WO | WO-99/22802 A1 | 5/1999 |
| WO | WO-99/56827 | 11/1999 |
| WO | WO-00/41726 A2 | 7/2000 |
| WO | WO-02/13788 A1 | 2/2002 |
| WO | WO-02/30512 A1 | 4/2002 |
| WO | WO-02/062420 A1 | 8/2002 |
| WO | WO-02/098508 A1 | 12/2002 |
| WO | WO-2005/030328 A2 | 4/2005 |
| WO | WO-2006/013390 A1 | 2/2006 |
| WO | WO-2007/090256 A1 | 8/2007 |
| WO | WO-2007/112427 A2 | 10/2007 |
| WO | WO-2009/003173 A1 | 12/2008 |
| WO | WO-2009/074811 A2 | 6/2009 |
| WO | WO-2009/131727 A2 | 10/2009 |
| WO | WO-2010/044879 A2 | 4/2010 |
| WO | WO-2010/128751 A2 | 11/2010 |
| WO | WO-2011/084722 A1 | 7/2011 |
| WO | WO-2011/124912 A1 | 10/2011 |
| WO | WO-2011/153599 A1 | 12/2011 |
| WO | WO-2012/086991 A2 | 6/2012 |
| WO | WO-2013/110021 A1 | 7/2013 |
| WO | WO-2014/064075 A1 | 5/2014 |
| WO | WO-2014/131115 A1 | 9/2014 |
| WO | WO-2014/147624 A1 | 9/2014 |
| WO | WO-2015/041919 A1 | 3/2015 |
| WO | WO-2017/066270 A1 | 4/2017 |
| WO | WO-2019/018408 A1 | 1/2019 |
| WO | WO-2024/209064 A1 | 10/2024 |
| WO | WO-2024/209073 A1 | 10/2024 |

OTHER PUBLICATIONS

A Pharmacokinetic Study of Levulan Kerastick (aminolevulinic acid HCl) for Topical Solution, 20%, Under Maximal Use Conditions, Clinical Study Report, DUSA Pharmaceuticals, Jul. 19, 2016, 69 pages.
A Phase 2 Study of Photodynamic Therapy With Levulan Topical Solution—Blue Light Versus Levulan Topical Solution Vehicle—Blue Light for the Treatment of Actinic Keratoses on the Upper Extremities, Clinical Study Report, DUSA Pharmaceuticals, Dec. 11, 2012, 80 pages.
A Phase 3 Study of Photodynamic Therapy With Levulan Kerastick Topical Solution—Blue Light Versus Topical Solution Vehicle—Blue Light for the Treatment of Actinic Keratoses on the Upper Extremities, Clinical Study Report, DUSA Pharmaceuticals, Mar. 1, 2017, 112 pages.
Complainant's Initial Statement Regarding the Public Interest, filed Jun. 25, 2024 in ITC Investigation No. 337-TA-1411.
Complaint filed Jun. 25, 2024 in *Sun Pharmaceutical Industries, Inc. v. Biofrontera Inc et al.*, 1:24-cv-11637 (D. Mass).
Complaint of Sun Pharmaceutical Industries, Inc. filed Jun. 25, 2024 in ITC Investigation No. 337-TA-1411.
Curriculum Vitae of Jose Sasian, Ph.D., filed Aug. 22, 2024 in IPR 2024-00874.
Declaration of Jose Sasian, Ph.D., filed Aug. 22, 2024 in IPR 2024-00874.
Declaration of Eric Bretschneider, Ph.D., filed Apr. 30, 2024 in IPR 2024-00874.
Declaration of Michael Ehrenreich, M.D., for filed Aug. 21, 2024 in IPR of 2024-01312.
Declaration of Robert E. Grove, Ph.D., filed Aug. 21, 2024 in IPR 2024-01312.

(56) References Cited

OTHER PUBLICATIONS

Office Action in U.S. Appl. No. 17/506,849 dated Sep. 6, 2024.
Full Prescribing Information of Levulan Kerastick, Mar. 2010.
Gold M. H. (Sep. 2008), "Therapeutic and Aesthetic Uses of Photodynamic Therapy Part two of a five-part series: Lasers and Light Treatments for Acne Vulgaris Promising Therapies", The Journal of Clinical and Aesthetic Dermatology, vol. 1, No. 3, p. 28-34.
Infringement Claim Chart for U.S. Pat. No. 11,697,028 filed Jun. 25, 2024 in *Sun Pharmaceutical Industries, Inc.* v. *Biofrontera Inc et al.*, 1:24-cv-11637 (D. Mass).
Notice of Reasons for Refusal on JP 2023-146114 Dtd Aug. 13, 2024 (15 pages) (with English Translation).
Pariser, David M. et al., Randomized Vehicle-Controlled Study of short Drug Incubation Aminolevulinic Acid Photodynamic Therapy for Actinic Keratoses of the Face or Scalp, American Society for Dermatologic Surgery, Inc., Mar. 2016, pp. 296-304.
Patent Owner's Preliminary Response filed Aug. 22, 2024 in IPR 2024-00874.
Petition for Inter Partes Review of U.S. Pat. No. 11,697,028 filed Apr. 30, 2024 (IPR 2024-00874).
Petition for Inter Partes Review of U.S. Pat. No. 11,697,028 filed Aug. 21, 2024 (IPR 2024-01312).
Schmieder, G. et al., A Multicenter, Randomized, Vehicle-Controlled Phase 2 Study of Blue Light Photodynamic Therapy With Aminolevulinic Acid HCl 20% Topical Solution for the Treatment of Actinic Keratoses on the Upper Extremities: The Effect of Occlusion During the Drug Incubation Period, Journal of Drugs in Dermatology, vol. 11, Issue 12, Dec. 2012, pp. 1483-1489.
Specimen for Beautylight, United States Trademark Serial No. 78214595, MDE Medizintechnik GmbH, Specimen submitted May 29, 2007.
Johanna T. H. M. van den Akker et al., "Effect of elevating the skin temperature during topical ALA application on in vitro ALA penetration through mouse skin and in vivo PpIX production in human skin" Photochem. Photobiol. Sci., 2004, 3, 263-267(Feb. 2004).
U.S. Appl. No. 17/854,066, filed Jun. 30, 2022, Willey, Andrea.
U.S. Appl. No. 17/876,224, filed Jul. 28, 2022, Lundahl, Scott et al.
U.S. Appl. No. 17/942,353, filed Sep. 12, 2022, Boyajian, Thomas et al.
Maisch et al., "Fluorescent Induction of Protoporphyrin IX by a New 5-Aminolevulinic Acid Nanoemulsion Used for Photodynamic Therapy in a Full-Thickness ex vivo Skin Model," Experimental Dermatology, 19, © 2009, e302-e305, published Jul. 2010.
Notice of Allowance in U.S. Appl. No. 17/487,698 Dtd Oct. 4, 2022, 6 pages.
USPTO Office Action in U.S. Appl. No. 17/876,224 Dtd Sep. 27, 2022, 20 pages.
Office Action in Japanese Application No. 2019-555822 mailed Nov. 1, 2022 and English translation thereof, 11 pages.
Touma, Yaar, Whitehead, Konnikov and Gilchrest, A trial of short incubation, broad-area photodynamic therapy for facial actinic keratoses and diffuse photodamage, Arch Dermatol. Jan. 2004; 140(1): 33-40.
Ang et al., "Photodynamic Therapy and Pain: A Systematic Review," Photodiagnosis and Photodynamic Therapy 19 (Jul. 2017) 308-344.
Kim et al. "In vivo skin absorption dynamics of topically applied pharmaceuticals monitored by fiber-optic diffuse reflectance spectroscopy," Spectrochimica Acta Part A 66, Mar. 2007, 768-772.
Mordon S, A Commentary on the Role of Skin Temperature on the Effectiveness of ALA-PDT in Dermatology, Photodiagnosis and Photodynamic Therapy (Accepted Aug. 2014).
Nishimura et al., "Iontophoretic Photosensitization of the Skin Re-evaluated by Colorimetric Imaging in Senile Patients," Bioimages 19, Jan. 2011, 1-6.
Warren et al., "Pain Associated with Aminolevulinic Acid-Photodynamic Therapy of Skin Disease," J Am Acad Dermatol., Dec. 2009 61(6): 1033-1043.

Willey et al., "Temperature-Modulated Photodynamic Therapy for the Treatment of Actinic Keratosis on the Extremities: A Pilot Study" Dermatol Surg; 40:1094-1102, Oct. 2014.
Ye et al. "Evaluation of Hydrogel Suppositories for Delivery of 5-Aminolevulinic Acid and Hematoporphyrin Monomethyl Ether to Rectal Tumors," Molecules, Oct. 2016, 21, 1347, 1-12.
Champeau et al. "Photodynamic therapy for skin cancer: How to enhance drug penetration?", Journal of Photochemistry and Photobiology B: Biology, vol. 197, Jul. 2, 2019.
Affidavit of Duncan Hall, Aug. 10, 2021.
Agostinis et al. Photodynamic therapy of cancer: an update. CA: A Cancer Journal for Clinicians. May 2011; 61(4):250-2.
Aktilite CL128 Operators Manual with Metvixia, Revised 2008.
Ameluz, Prescribing Information (2016).
Australian Examination Report, Application No. 2020267186, Nov. 19, 2021, 6 pages.
Australian Examination Report, Application No. 2020267186, Feb. 3, 2022, 4 pages.
Australian Examination Report, Application No. 2021107564, Apr. 4, 2022, 4 pages.
Australian Office Action, Application No. 2019200152, Nov. 11, 2019, 9 pages.
Berardesca E, Vignoli GP, Fideli D, Maibach H. Effect of occlusive dressings on the stratum corneum water holding capacity. The American Journal of the Medical Sciences. Jul. 1992;304(1):25-28.
Bissonnette R. Photodynamic therapy. In: Gold M.H., editor. Photodynamic Therapy in Dermatology. Springer Science and Business Media, LLC; New York, NY, USA: 2011. pp. 221-229.
Blu-U, Operating Manual (2006).
Braathen, Lasse R., et al. "Guidelines on the Use of Photodynamic Therapy for Nonmelanoma Skin Cancer: an International Consensus." Journal of the American Academy of Dermatology 56.1, Jan. 2007, pp. 125-143.
Britannica, The Editors of Encyclopaedia, "Gel: Physics and Chemistry", 4 pages, Jul. 20, 1998, and "Gel: Additional Information", 1 page, Available on line at: https://www.britannica.com/science/gel and https://www.britannica.com/science/gel/additional-info#history.
Calderhead RG. Light-emitting diode phototherapy in dermatological practice in lasers in dermatology and medicine. Lasers in Dermatology and Medicine. Aug. 2011:231-265.
CV of Dr. Howard Rogers MD, PHD.
Daniel Barolet et al., Radiant Near Infrared Light Emitting Diode Exposure as Skin Preparation to Enhance Photodynamic Therapy Inflammatory Type Acne Treatment Outcome, Lasers in Surgery and Medicine vol. 42, No. 2, Feb. 1, 2010, pp. 171-178.
Declaration of Dr. Howard Rogers MD, PHD, Oct. 19, 2021.
Dragieva, G. et al., "A Randomized Controlled Clinical Trial of Topical Photodynamic Therapy with Methyl Aminolaevulinate in the Treatment of Actinic Keratoses in Transplant Recipients." British Journal of Dermatology 151.1, Jul. 2004, pp. 196-200.
DUSA Levulan Press Release, Dec. 6, 1999.
European Medicines Agency CHMP Assessment Report (excerpts), Oct. 20, 2011.
European Office Action, Application No. 16787667.1, Sep. 24, 2019, 5 pages.
Extended European Search Report, Application No. 18835929.3, Mar. 12, 2021, 10 pages.
Extended European Search Report, Application No. 20214586.8, Jun. 2, 2021, 8 pages.
Fauteck Europe PMC Website Database Listing, Oct. 25, 2007.
Fauteck JD, Ackermann G, Birkel M, Breuer M, Moor AC, Ebeling A, Ortland C. Fluorescence characteristics and pharmacokinetic properties of a novel self-adhesive 5-ALA patch for photodynamic therapy of actinic keratoses, 2008.
Fehr et al., Photodynamic Therapy of Vulvar and Vaginal Condyloma and Intraepithelial Neoplasia Using Topically Applied 5-Aminolevulinic Acid, Lasers in Surgery and Medicine, 2002, 30:273-279, 7 pages.
Fehr et al., Selective Photosensitizer Distribution in Vulvar Condyloma Acuminatum After Topical Application of 5-Aminolevulinic Acid, Am. J. Obstet. Gynecol., vol. 174(3), Mar. 1996, pp. 951-957.
GLAD.com.au: "GLAD History", 2012, [online] URL: http://www.glad.com.au/about-glad/glad-history/, retrieved online Nov. 8, 2019.

(56) References Cited

OTHER PUBLICATIONS

Harris DR. Percutaneous absorption and the surface area of occluded skin: a scanning electron microscopic study. British Journal of Dermatology. 1974; 91(27-32).
Hongcharu W., Taylor C., Chang, Y., Aghasi, D., Suthamjariya, K., Anderson, R. Topical ALA-photodynamic therapy for the treatment of acne vulgaris. J Invest Dermatol. Aug. 2000;115(2):183-92.
Hurlimann et al., Photodynamic Therapy of Superficial Basal Cell Carcinomas Using Topical 5-Aminolevulinic Acid in a Nanocolloid Lotion, Pharmacology and Treatment, Dermatology 197, 1998, pp. 248-254.
International Patent Reviews, LLC review of U.S. Pat. No. 10,357,567 dated Jul. 26, 2021.
International Preliminary Report on Patentability, PCT/US2016/056572, Apr. 26, 2018, 9 pages.
International Preliminary Report on Patentability, PCT/US2018/027070, Oct. 24, 2019, 10 pages.
International Search Report and Written Opinion International Application No. PCT/US2018/027070, Oct. 16, 2018, 18 pages.
International Search Report from PCT/US2018/042505, issued Oct. 2, 2018.
Japanese Office Action and English translation, Application No. 2019-555822, Jan. 11, 2022, 13 pages.
Japanese Office Action and English Translation, Application No. JP 2020-503004, Dated Aug. 2, 2022, 6 pages.
Jeffes E., Mccullough J., Weinstein G., Fergin P., Nelson J., Shull T., Simpson K., Bukaty L., Hoffman W., Fong N. Photodynamic therapy of actinic keratosis with topical 5-aminolevulinic acid. A pilot dose-ranging study. Arch Dermatol. 1997.
Johanna T.H.M. Van Den Akker et al., Effect of Elevating the Skin Temperature During Topical ALA Application on in vitro ALA penetration Through Mouse Skin and in vivo PpIX production in Human Skin, Photochemical and Photobiological Sciences, Royal Society of Chemistry, Cambridge, GB, vol. 3, No. 3, Mar. 1, 2004, pp. 263-267.
Kurwa, Habib A., et al., "A Randomized Paired Comparison of Photodynamic Therapy and Topical 5-Fluorouracil in the Treatment of Actinic Keratoses." Journal of the American Academy of Dermatology 41.3, Sep. 1999, pp. 414-418.
Letter to UVBiotek, LLC dated Jul. 28, 2017 Re: K170187, Trade/Device Name: Photodynamic Therapy Device, available at https://www.accessdata.fda.gov/cdrh_docs/pdf17/K170187.pdf (accessed Apr. 30, 2020).
Levulan, Label (2002).
Levulan, Label (2009).
Maccormack, Mollie A., "Photodynamic Therapy in Dermatology: An Update on Applications and Outcomes." Seminars in Cutaneous Medicine and Surgery. vol. 27, No. 1, WB Saunders, Mar. 2008, pp. 52-62.
Maisch et al., Fluorescence Induction of Protoporphyrin IX by a New 5-Aminolevulinic Acid Nanoemulsion Used for Photodynamic Therapy in a Full-Thickness ex vivo Skin Model, Experimental Dermatology, 19, 2009, pp. e302-e305.
McLaren G. Photodynamic therapy. In: Pfenninger and Fowler's procedures for primary care. Third Ed. Mosby Elsevier; Philadelphia, PA: 2011. pp. 397-400.
News article entitled DUSA Pharmaceuticals To Pay U.S. $20.75 Million To Settle False Claims Act Allegations Relating To Promotion Of Unsupported Drug Administration Process, Aug. 24, 2020.
Notice of Allowance, U.S. Appl. No. 15/487,991, Jan. 15, 2020, 11 pages.
Notice of Allowance, U.S. Appl. No. 15/487,991, Oct. 2, 2019, 16 pages.
Notice of Allowance, U.S. Appl. No. 17/487,698, Apr. 29, 2022, 11 pages.
Nucci et al., Treatment of Anogenital Condylomata Acuminata with Topical Photodynamic Therapy: Report of 14 Cases and Review, International Journal of Infectious Diseases, 14S, 2010, pp. e280-e282.
Ozog, David M., et al., "Photodynamic Therapy: A Clinical Consensus Guide." Dermatologic Surgery 42.7, Jul. 2016, pp. 804-827.
Palm M., Goldman PM. Aminolevulinic acid: actinic keratosis and photorejuvenation. In: Gold M.H., editor. Photodynamic Therapy in Dermatology. Springer Science and Business Media, LLC. Nov. 2011:5-30.
Partial International Search, Annex to Form PCT/ISA/206, International Application No. PCT/US2018/027070, Jul. 19, 2018, 10 pages.
Petition for Inter Partes Review Under 35 U.S.C. 312, Oct. 19, 2021.
Petras Juzenas et al., Uptake of Topically Applied 5-Aminolevulinic Acid and Production of Protoporphyrin IX in Normal Mouse Skin: Dependence on Skin Temperature, Photochemistry and photobiology, vol. 69, No. 4, Apr. 1, 1999, pp. 478-481.
Reinhold et al., A Randomized, Double-Blind, Phase III, Multicentre Study to Evaluate the Safety and Efficacy of BF-200 ALA (Ameluz®) vs. Placebo in the Field-Directed Treatment of Mild-to-Moderate Actinic Keratosis with Photodynamic Therapy (PDT) When Using the BF-RhodoLED® Lamp, British Journal of Dermatology, 175(4): 696-705, Feb. 27, 2016, 10 pages.
Rick K, Sroka R, Stepp H, Kriegmair M, Huber RM, Jacob K, Baumgartner R. Pharmacokinetics of 5-aminolevulinic acidinduced protoporphyrin IX in skin and blood. J Photochem Photobiol B. Oct. 1997;40(3):313-9.
Sakamoto FH, Torezan L, Anderson RR. Photodynamic therapy for acne vulgaris: a critical review from basics to clinical practice: part II. Understanding parameters for acne treatment with photodynamic therapy. J Am Acad Dermatol. Aug. 2010;63(2):195-211.
Sotiriou E, Apalla Z, Maliamani F, Zaparas N, Panagiotidou D, Ioannides D. Intraindividual, right-left comparison of topical 5-aminolevulinic acid photodynamic therapy vs. 5% imiquimod cream for actinic keratoses on the upper extremities, 2009.
Sotiriou Pubmed Website Database Listing, Sep. 23, 2009.
Third Party Submission filed in U.S. Appl. No. 17/109,311, Jun. 21, 2021, 21 pages.
USPTO Advisory Action, U.S. Appl. No. 15/487,991, May 15, 2018, 5 pages.
USPTO Interview Summary, U.S. Appl. No. 15/487,991, Sep. 22, 2017, 4 pages.
USPTO Non-Final Office Action, U.S. Appl. No. 16/631,205, Mar. 3, 2022, 31 pages.
USPTO Notice of Allowance, U.S. Appl. No. 15/292,731, Nov. 14, 2019, 12 pages.
USPTO Notice of Allowance, U.S. Appl. No. 16/438,702, Mar. 22, 2021, 14 pages.
USPTO Notice of Allowance, U.S. Appl. No. 16/438,702, May 20, 2021, 10 pages.
USPTO Notice of Allowance, U.S. Appl. No. 17/009,871, Jul. 22, 2021, 14 pages.
USPTO Notice of Allowance, U.S. Appl. No. 17/109,311, Aug. 10, 2021, 14 pages.
USPTO Office Action, U.S. Appl. No. 15/487,991, Jul. 31, 2018, 20 pages.
USPTO Office Action, U.S. Appl. No. 15/487,991, Apr. 9, 2019, 27 pages.
USPTO Office Action, U.S. Appl. No. 15/487,991, Jun. 12, 2017, 22 pages.
USPTO Office Action, U.S. Appl. No. 15/487,991, Feb. 6, 2018, 19 pages.
USPTO Office Action, U.S. Appl. No. 16/438,702, Oct. 13, 2020, 17 pages.
USPTO Office Action, U.S. Appl. No. 16/791,004, Oct. 25, 2021, 26 pages.
USPTO Office Action, U.S. Appl. No. 16/808,631, Jan. 21, 2022, 28 pages.
USPTO Office Action, U.S. Appl. No. 17/009,871, Dec. 2, 2020, 15 pages.
USPTO Office Action, U.S. Appl. No. 17/109,311, Jul. 20, 2021, 17 pages.
USPTO Office Action, U.S. Appl. No. 17/487,698, Dec. 17, 2021, 21 pages.
USPTO Office Action, U.S. Appl. No. 17/009,871, Mar. 23, 2021, 9 pages.

(56) References Cited

OTHER PUBLICATIONS

USPTO Office Action, U.S. Appl. No. 17/109,311, Mar. 2, 2021, 16 pages.
Wachowska et al., Aminolevulinic acid (ALA) as a prodrug in photodynamic therapy of cancer. Molecules. May 2011; 16(5): 4140-4164.
Webpage printout, Hill Laboratories Company, "Aklarus Phototherapy Treatment System with Red, Blue and Infrared Wavelengths by Hill Therapeutics," available at https://hilllabs.com/therapeutics/Aklarus-Photo-Therapy-System.php (accessed Apr. 30, 2020).
Willey A, Anderson RR, Sakamoto FH. Temperature-modulated photodynamic therapy for the treatment of actinic keratosis on the extremities. Dermatologic Surgery. Oct. 2014;40(10):1094-1102.
Willey et al., American Society for Laser Medicine and Surgery Abstracts, #147, Ultra Fast Thermal PDT for Facial AKs: Proof of Concept Study, Mar. 2017, 2 pages.
Willey Pubmed Website Database Listing, Oct. 2014.
Wolf, Peter, et al., "Topical Photodynamic Therapy With Endogenous Porphyrins After Application of 5-Aminolevulinic Acid: An Alternative Treatment Modality for Solar Keratoses, Superficial Squamous Cell Carcinomas, and Basal Cell Carcinomas?" Journal of the American Academy of Dermatology 28.1, Jan. 1993, pp. 17-21.
Zhang et al., "Topical 5-Aminolevulinic Photodynamic Therapy with Red Light vs Intense Pulsed Light for the Treatment of Acne Vulgaris _ A Spilit [sic] Face, Randomized, Prospective Study," Dermato-Endocrinology, 2018, vol. 9, No. 1, e1375634 (9 pages).
"About Actinic Keratosis (Keratoses)"; SOMA Skin & Laser; https://somalaser.com/skin-conditions/actinic-keratosis/; accessed Nov. 21, 2024; 2 pages.
"BLU-U - Blue Light for Acne and Actinic Keratosis"; SOMA Skin & Laser; https://somalaser.com/blu- for-acne; Nov. 21, 2024; 2 pages.
"Exhibit 10C: Technical Domestic Industry Claim Chart for U.S. Pat. No. 11,697,028 ("028 Patent")—Sun Pharmaceutical Industries, Inc.'s BLU-U Blue Light Photodynamic Therapy Illuminator—Model 4170E ("Blu-U 4170E") device, individually and in combination with Levulan Prescription Medicine"; Jun. 25, 2024; 172 pages.
"How Levulan Kerastick BLU-U Works"; How It Works—Levulan Kerastick (aminolevulinic acid Hci) Blu-U; https://www.levulanhcp.com/how-it-works; accessed Nov. 21, 2024; 4 pages.
"How much space does a BLU-U require?"; Levulan Kerastick (aminolevulinic acid HCI) for Topical Solution, 20%; https://www.mydrugrep.com/mobile-campaigns/Levulan_V13a_01a/space_requirements.html; accessed Nov. 21, 2024; 3 pages.
"How to Use Levulan Kerastick—BLU-U"; How To Use - Levulan Kerastick (aminolevulinic acid HCI) Blu-U; https://www.levulanhcp.com/how-to-use; accessed on Nov. 25, 2024; 6 pages.
"Michael Ehrenreich, Md, Faad, Dermatologist and Medical Director, SOMA Skin & Laser, Millburn, NJ"; https://somolaser.com/dr-michael-ehrenreich-md-millburn-dermatologist/; accessed Nov. 21, 2024; 3 pages.
"Photodynamic Therapy for Acne"; SOMA Skin & Laser; https://somalaser.com/photodynamic-therapy/; accessed Nov. 21, 2024; 1 page.
"Photodynamic Therapy for Actinic Keratoses and Skin Cancer"; SOMA Skin & Laser; https://somalaser.com/photodynamic-therapy-for-actinic-keratoses-and-skin-cancer/; accessed Nov. 21, 2024; 2 pages.
"Photodynamic Therapy for Skin Conditions"; SOMA Skin & Laser; https://www.somalaser.com/photodynamic-therapy-for-skin-conditions/; accessed Nov. 21, 2024; 4 pages.
"Photodynamic Therapy"; Photodynamic Therapy (PDT) - Dr. Heather Roberts; https://www.drheatherroberts.com/procedures-and-treatments/photodynamic-therapy-pdt-for-skin-cancer/; accessed Nov. 21, 2024; 3 pages.
"Proven Results for Levulan Kerastick (aminolevulinic acid HCI) Blu-U"; https://www.levulanhcp.com/efficacy#isi-homepage-levulanhcp; accessed Nov. 25, 2024; 4 pages.
"Proximate"; Merriam Webster; https://www.merriam-webster.com/dictionary/proximate; accessed Oct. 22, 2024; 1 page.
"Recess"; Merriam-Webster's Collegiate Dictionary, Eleventh Edition; Meriam-Webster, Incorporated, Springfield, Massachusetts; 2005; p. 1038.
"Recess"; Merriam-Webster's Online Dictionary; https://www.merriam-webster.com/dictionary/recess; accessed on Oct. 17, 2024; 11 pages.
"Recess"; Oxford English Dictionary; Oxford University Press; 2024; 12 pages.
"Recess"; The American Heritage Dictionary; https://ahdictionary.com/word/search.html?q=recess; as accessed on Oct. 17, 2024; 3 pages.
"Strike AKs with Confidence"; Levulan Kerastick (aminolevulinic acid HCI) Blu-U—HCP Home Page; https://www.levulanhcp.com/; accessed on Nov. 25, 2024; 4 pages.
"Treatment Landscape—Levulan Kerastick (aminolevulinic acid HCI) Blu-U"; https://www.levulanhcp.com/treatment-landscape; accessed Nov. 21, 2024; 5 pages.
"Treat What Happened Yesterday, Today—Levulan Kerastick BLU-U"; Jan. 2021; 16 pages.
Allison, Ron R. et al.; "The future of photodynamic therapy in oncology"; Future Oncol, vol. 2, No. 1; Feb. 2006; pp. 53-71.
Amended Verified Complaint of Complainant Sun Pharmaceutical Industries, Inc., U.S. International Trade Commission Investigation 337-TA-1411, dated Oct. 29, 2024, 56 pages.
Avci, Pinar et al.; "Low-level laser (light) therapy (LLT) in skin: stimulating, healing, restoring"; Seminars in Cutaneous Medicine and Surgery, vol. 32, No. 1; Mar. 2013; pp. 41-52.
Barolet, Daniel; "Light-Emitting Diodes (LEDs) in Dermatology"; Seminars in Cutaneous Medicine and Surgery, vol. 27, No. 4; Dec. 2008; pp. 227-238.
Bourget, C. Michael; "An Introduction to Light-emitting Diodes"; HortScience, vol. 43, No. 7; Dec. 2008; pp. 1944-1946.
Brancaleon, L et al., "Laser and Non-Laser Light Sources for Photodynamic Therapy"; Lasers Med. Sci., vol. 17, No. 3; Feb. 2002; pp. 173-186.
Calderhead, R. Glen; "The Photobiological Basics Behind Light-Emitting Diode (LED) Phototherapy"; Laser Therapy, vol. 16, No. 2; Jan. 2007; pp. 97-108.
Chen, Hsi-Chao et al.; "Investigation of illumination efficiency on the LED therapy with different array types"; Proceedings of SPIE—The International Society for Optical Engineering, vol. 7422; Aug. 2009; 8 pages.
Complainant Sun Pharmaceutical Industries, Inc.'s Corrected Claim Construction Brief, U.S. International Trade Commission Investigation 337-TA-1411, with cover letter dated Nov. 21, 2024, 42 pages.
Complainant Sun Pharmaceutical Industries, Inc.'s Supplemental Objections and Responses to Respondents' First and Second Set of Interrogatories (Nos. 7, 9, 18-25); U.S. International Trade Commission Investigation No. 337-TA-1411; Dec. 18, 2024; 183 pages.
Complainant Sun Pharmaceutical Industries, Inc.'s Initial Statement Regarding the Public Interest, Biofrontera Inc et al. v. Sun Pharmaceutical Industries, Inc .; U.S. International Trade Commission, Jun. 25, 2024; 6 pages.
Complainant Sun Pharmaceutical Industries, Inc.'s Letter regarding IPR Decision of Non-Institution for IPR2024-01312 appending copy of Decision of Non-Institution, submitted in U.S. International Trade Commission Investigation No. 337-TA-1411, dated Nov. 21, 2024, 26 pages.
Complainant Sun Pharmaceutical Industries, Inc.'s Opening Claim Construction Brief; U.S. International Trade Commission Investigation No. 337-TA-1411; Oct. 31, 2024; 41 pages.
Complainant Sun Pharmaceutical Industries, Inc.'s Responsive Claim Construction Brief, U.S. International Trade Commission Investigation 337-TA-1411, Nov. 15, 2024; 23 pages.
Curriculum Vitae of Heather J. Roberts, Md, Faad; filed Nov. 27, 2024 in IPR2024-01312; U.S. Pat. No. 11,697,028, 3 pages.
Decision Denying Institution of Inter Partes Review; IPR2024-00874, U.S. Pat. No. 11,697,028; Nov. 12, 2024; 22 pages.

(56) References Cited

OTHER PUBLICATIONS

Declaration of Dr. Nan Marie Jokerst Regarding Claim Construction; U.S. International Trade Commission Investigation No. 337-TA-1411; executed on Oct. 3, 2024; 69 pages.
Declaration of Heather J. Roberts, M.D., Faad; *Biofrontera Inc. Biofrontera Bioscience GmbH, Biofrontera Pharma GmbH and Biofrontera AG v. Sun Pharmaceutical Industries, Inc.*; IPR2024-01312, U.S. Pat. No. 11,697,028; Nov. 23, 2024; 23 pages.
Declaration of Jose Sasian; Biofrontera Inc., Biofrontera Bioscience GmbH, Biofrontera Pharma GmbH, and Biofrontera AG v. Sun Pharmaceutical Industries, Inc .; IPR2024-01312, U.S. Pat. No. 11,697,028, filed Nov. 27, 2024; 101 pages.
Expert Declaration of Michael Ehrenreich, MD, for Inter Partes Review of U.S. Pat. No. 11,446,512; executed on Dec. 11, 2024; 25 pages.
Expert Declaration of Robert E. Grove, Ph.D., for Inter Partes Review of U.S. Pat. No. 11,446,512; executed on Dec. 18, 2024; 106 pages.
Expert Report of Robert E. Grove, Ph. D. in Support of Respondents Biofrontera Inc., Biofrontera Pharma GmbH, Biofrontera Bioscience GmbH, and Biofrontera AG's Opening Claim Construction Brief; U.S. International Trade Commission Investigation No. 337-TA-1411; Oct. 3, 2024; 44 pages.
Finlayson, Louise et al., "Depth Penetration of Light into Skin as a Function of Wavelength from 200 to 1000 nm"; Photochemistry and Photobiology, vol. 98, No. 4; Nov. 2021; pp. 974-981.
Gold, Michael H. et al.; "5-Aminolevulinic Acid Photodynamic Therapy: Where We Have Been and Where We Are Going"; Dermatol. Surg., vol. 30, No. 8; Aug. 2004; pp. 1077-1084.
Gold, Michael H.; "Acne vulgaris: lasers, light sources and photodynamic therapy—an update 2007"; Expert Rev. Anti Infect. Ther., vol. 5, No. 6; Dec. 2007; pp. 1059-1069.
Gold, Michael H.; (1); "Therapeutic and Aesthetic Uses of Photodynamic Therapy: Part one of a five- part series: The Use of Photodynamic Therapy in the Treatment of Actinic Keratoses and in Photorejuvenation"; Journal of Clinical and Aesthetic Dermatology, vol. 1, No. 2; Jul. 2008; pp. 32-37.
Gold, Michael H.; (2); "Therapeutic and Aesthetic Uses of Photodynamic Therapy: Part two of a five- part series: Lasers and Light Treatments for Acne Vulgaris: Promising Therapies"; Journal of Clinical and Aesthetic Dermatology, vol. 1, No. 3; Sep. 2008; pp. 28-34.
Gold, Michael H.; (3); "Therapeutic and Aesthetic Uses of Photodynamic Therapy: Part three of a five-part series: Chemoprevention utilizing ALA-PDT", Journal of Clinical and Aesthetic Dermatology, vol. 1, No. 4; Nov. 2008; pp. 26-32.
Gold, Michael H.; (4); "Therapeutic and Aesthetic Uses of Photodynamic Therapy: Part four of a five-part series: ALA-PDT in Clinical Practice: How One Clinician Performs This Procedure"; Journal of Clinical and Aesthetic Dermatology, vol. 2, No. 1; Jan. 2009; pp. 32-35.
Gold, Michael H.; (5); "Therapeutic and Aesthetic Uses of Photodynamic Therapy: Part five of a five-part series: ALA-PDT and MAL-PDT: What Makes Them Different"; Journal of Clinical and Aesthetic Dermatology, vol. 2, No. 2; Feb. 2009; pp. 44-47.
Gorse, Christopher et al.; A Dictionary of Construction, Surveying and Civil Engineering; Oxford University Press, Oxford, United Kingdom; ISBN 978-0-19-953446-3; 2012; 503 pages.
Hino, Hitoshi et al., "5-Aminolevulinic acid-mediated photodynamic therapy using light-emitting diodes of different wavelengths in a mouse model of peritoneally disseminated gastric cancer"; Journal of Surgical Research, vol. 185; Jun. 2013; pp. 119-126.
Joint Statement Identifying Accused Products, U.S. International Trade Commission Investigation No. 337-TA-1411, Dec. 4, 2024, 5 pages.
Juzeniene, Asta et al.; "Effectiveness of different light sources for 5-aminolevulinic acid photodynamic therapy"; Lasers in Medical Science, vol. 19; Oct. 2004; pp. 139-149.
Kalisiak, Michal S. et al.; "Photodynamic Therapy for Actinic Keratoses"; Dermatol. Clin., vol. 25, No. 1; Jan. 2007; pp. 15-23.

Kernel Medical Equipment Co., Ltd, "PDT Led Light Therapy Machine For skin rejuvenation KN-7000A," @ 2018, accessed at https://www.kernelmedint.com/product/pdt-led-light-therapy-machine-for-skin-rejuvenation-kn-7000a on Nov. 13, 2024.
Ko, Dong-Yeob et al.; "Comparative Study of Photodynamic Therapy with Topical Methyl Aminolevulinate versus 5-Aminolevulininc Acid for Facial Actinic Keratosis with Long-Term Follow-Up"; Ann. Dermatol., vol. 26, No. 3; Jun. 2014; pp. 321-331.
Langmack, Keith et al.; "Topical photodynamic therapy at low fluence rates - theory and practice"; Journal of Photochemistry and Photobiology B: Biology, vol. 60, No. 1; Apr. 2001; pp. 37-43.
Larivee, Brian; "RE: Inv. 1411—M&C re: Claim Construction"; email from Brian Larivee to Tuhin Ganguly et al., relating to U.S. International Trade Commission Investigation No. 337-TA-1411, Oct. 3, 2024; 5 pages.
Levulan kerastick-aminolevulinic acid hydrochloride, FDA Label, 2000, 2003, 2009, 2010; 12 pages.
Lighting-Gallery.net; My lights/completely clear/uncoated Sylvania 28W T5 He demonstration tube; https://www.lighting-gallery.net/gallery/displayimage.php?album=1601&pos=188&pid=211863; accessed on Oct. 30, 2024; 3 pages.
Ma, Li et al.; "Low-dose topical 5- aminolevulinic acid photodynamic therapy in the treatment of different severity of acne vulgaris"; Photodiagnosis and Photodynamic Therapy, vol. 10, No. 4; Dec. 2013; pp. 583-590.
Marrero, Allison et al.; "Aminolevulinic Acid-Photodynamic Therapy Combined with Topically Applied Vascular Disrupting Agent Vadimezan Led to Enhanced Antitumor Responses"; Photochem. Photobiol., vol. 87, No. 4; Jul. 2011; pp. 910-919.
Matthews, Y.I. et al.; "Topical photodynamic therapy is immunosuppressive in humans"; British Journal of Dermatology, vol. 162, No. 3; Mar. 2010; pp. 637-641.
Metvixia methyl aminolevulinate cream, 16.8%; FDA Label; Jun. 2008, 40 pages.
Moan Johan et al.; "The Temperature Dependence of Protoporphyrin IX Production in Cells and Tissues"; Photochemistry and Photobiology, vol. 70, No. 4; Oct. 1999; pp. 669-673.
Moseley, Harry; "Light distribution and calibration of commercial PDT LED arrays"; Photochem. Photobiol. Sci., vol. 4; Sep. 2005; pp. 911-914.
Ndjiongue, Alain Richard et al.; "Visible Light Communications (VLC) Technology"; Wiley Encyclopedia of Electrical and Electronics Engineering, J.G. Webster (Ed.); https://doi.org/10.1002/047134608X.W8267; Jun. 2015; 24 pages.
Notice of Prior Art; U.S. International Trade Commission Investigation No. 337-TA-1411, Sep. 23, 2024, 18 pages.
Omnilux Blue Light Acne Treatment Brisbane & Gold Coast, Beauty by Laser; YouTube Video, https://www.youtube.com/watch?v=V8F-R-pw16Y; May 31, 2011; 2 pages.
Patent Owner's Preliminary Response; *Biofrontera Inc., Biofrontera Bioscience GmbH, Biofrontera Pharma GmbH, and Biofrontera AG v. Sun Pharmaceutical Industries, Inc.*; IPR2024-01312, U.S. Pat. No. 11,697,028; Nov. 27, 2024; 81 pages.
Patent Owner's Response to Petitioner's Notice Regarding Parallel Petitions; *Biofrontera Inc., Biofrontera Bioscience GmbH, Biofrontera Pharma GmbH, and Biofrontera AG v. Sun Pharmaceutical Industries, Inc.*; IPR2024-01312, U.S. Pat. No. 11,697,028; Nov. 27, 2024; 8 pages.
Peng, Qian et al.; "5-Aminolevulinic Acid-Based Photodynamic Therapy: Clinical Research and Future Challenges"; Cancer, vol. 79, No. 12; Jun. 1997; pp. 2282-2308.
Petition for Inter Partes Review of U.S. Pat. No. 11,446,512 under 35 U.S.C. 311-319 and 37 C.F.R. 42.100 et seq.; *Biofrontera Inc., Biofrontera Bioscience GmbH, Biofrontera Pharma GmbH, and Biofrontera AG v. Sun Pharmaceutical Industries, Inc.*; IPR2025-00287, Patent No. 11,446,512; Dec. 27, 2024; 89 pages.
Petitioner's Notice Regarding Parallel Petitions, *Biofrontera Inc., Biofrontera Bioscience GmbH, Biofrontera Pharma GmbH, and Biofrontera AG v. Sun Pharmaceutical Industries, Inc.*, IPR2024-01312, U.S. Pat. No. 11,697,028; Aug. 21, 2024; 7 pages.

(56) References Cited

OTHER PUBLICATIONS

Plaintiff's Infringement Contentions submitted as Exhibit 3 attached to complaint filed in *Sun Pharmaceutical Industries, Inc.* v. *Biofrontera Bioscience GmbH et al.*; Civil Action No. 1:24-cv-11637 (D. Mass); filed on Jun. 25, 2024; 56 pages.

Rebuttal Declaration of Dr. Nan Marie Jokerst Regarding Claim Construction, U.S. International Trade Commission Investigation No. 337-TA-1411; Oct. 17, 2024; 45 pages.

Rebuttal Expert Report of Robert E. Grove, Ph.D. in Support of Respondents Biofrontera Inc., Biofrontera Pharma GmbH, Biofrontera Bioscience GmbH, and Biofrontera AG's Opening Claim Construction Brief; U.S. International Trade Commission Investigation No. 337-TA-1411; Oct. 17, 2024; 24 pages.

Respondents Biofrontera Inc., Biofrontera Pharma GmbH, Biofrontera Bioscience GmbH, and Biofrontera AG's Response to Complainant's Amended Complaint and the Amended Notice of Investigation, U.S. International Trade Commission Investigation 337-TA-1411, dated Dec. 11, 2024, 38 pages.

Respondents Biofrontera Inc., Biofrontera Pharma GmbH, Biofrontera Bioscience GmbH, and Biofrontera AG's Responsive Claim Construction Brief (public version); U.S. International Trade Commission Investigation No. 337-TA-1411; dated Nov. 15, 2024; filed on Nov. 22, 2024; 26 pages.

Respondents Biofrontera Inc., Biofrontera Pharma GmbH, Biofrontera Bioscience GmbH, and Biofrontera AG's Responsive Claim Construction Brief, U.S. International Trade Commission Investigation 337-TA-1411, dated Nov. 15, 2024, 169 pages.

Respondents Biofrontera Inc., Biofrontera Pharma GmbH, Biofrontera Bioscience GmbH, and Biofrontera AG's Opening Claim Construction Brief, U.S. International Trade Commission, U.S. International Trade Commission Investigation No. 337-TA-1411; Oct. 31, 2024; 42 pages.

Respondents Biofrontera Inc., Biofrontera Pharma GmbH. Biofrontera Bioscience GmbH, and Biofrontera AG's Opening Claim Construction Brief (public version), U.S. International Trade Commission Investigation No. 337-TA-1411, dated Oct. 31, 2024; filed on Nov. 22, 2024; 42 pages.

Respondents' Fifth Supplemental Responses to Complainant's First Set of Interrogatories (Nos. 31, 32, 34, and 41), U.S. International Trade Commission Investigation No. 337-TA-1411; Dec. 4, 2024; 197 pages.

Respondents' Response To The Complaint And Notice Of Investigation, dated Sep. 3, 2024, U.S. International Trade Commission Investigation No. 337-TA-1411, 39 pages.

Sun Pharmaceutical Industries, Inc.'s Complaint for Patent Infringement; *Sun Pharmaceutical Industries, Inc.* v. *Biofrontera Bioscience GmbH et al.*; Civil Action No. 1:24-cv-11637; U.S. District Court for the District of Massachusetts; filed on Jun. 25, 2024; 32 pages.

Supplemental Expert Report of Robert E. Grove, Ph.D. in Support of Respondents Biofrontera Inc., Biofrontera Pharma GmbH, Biofrontera Bioscience GmbH, and Biofrontera AG's Opening Claim Construction Brief; U.S. International Trade Commission Investigation No. 337-TA-1411; Oct. 17, 2024; 18 pages.

Tao, Shi-qin et al.; "Low-Dose Topical 5- Aminolevulinic Acid Photodynamic Therapy in the Treatment of Different Severity of Acne Vulgaris"; Cell Biochem. Biophys., vol. 73; May 27, 2015; pp. 701-706.

Verified Complaint of Sun Pharmaceutical Industries, Inc. under Section 337 of the Tariff Act of 1930, as Amended; U.S. International Trade Commission Investigation No. 337-TA-1411; filed Jun. 25, 2024; 53 pages.

Wan, Marilyn T et al.; "Current evidence and applications of photodynamic therapy in dermatology"; Clinical, Cosmetic and Investigational Dermatology, vol. 7, May 2014; pp. 145-163.

Wang, Xiu-Li et al.; "Topical Ala Pdt for the treatment of severe acne vulgaris"; Photodiagnosis and Photodynamic Therapy, vol. 7; Feb. 2010; pp. 33-38.

Wilson, Brian C. et al.; "The physics, biophysics and technology of photodynamic therapy"; Phys. Med. Biol., vol. 53; Apr. 2008; R61-R109.

Decision Granting Institution of Inter Partes Review; IPR2024-01312; U.S. Pat. No. 11,697,028; Feb. 24, 2025; 25 pages.

Order No. 18, Construing Certain Claim Terms, Inv. No. 337-TA-1411, In The Matter Of Certain Photodynamic Therapy Systems, Components Thereof, And Pharmaceutical Products Used In Combination With The Same, dated Mar. 4, 2025 (Public Version).

* cited by examiner

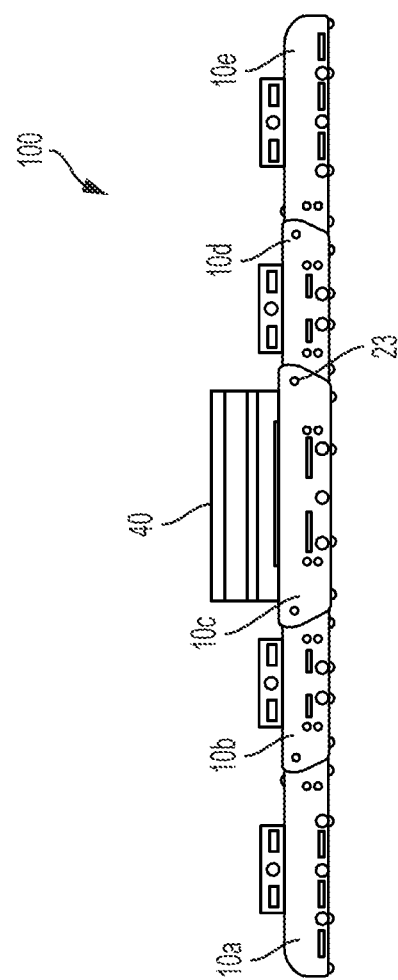
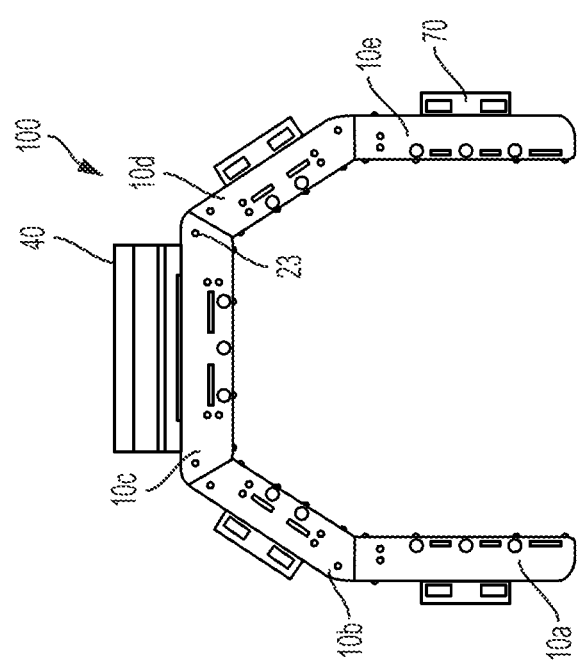

ADJUSTABLE ILLUMINATOR FOR PHOTODYNAMIC THERAPY AND DIAGNOSIS

CROSS-REFERENCE TO RELATED APPLICATIONS

This application is a continuation of U.S. application Ser. No. 16/791,004, filed Feb. 14, 2020, which is a divisional application of U.S. application Ser. No. 15/292,731, filed Oct. 13, 2016, now granted as U.S. Pat. No. 10,589,122, which claims the benefit of priority to U.S. Provisional Application No. 62/241,902 filed on Oct. 15, 2015, the entire contents of all of which are incorporated herein by reference.

FIELD

The invention relates generally to an adjustable illuminator that provides a uniform distribution of visible light in a number of configurations and is suitable for use in photodynamic therapy and diagnosis.

BACKGROUND

Photodynamic therapy (PDT), photodynamic diagnosis (PD), or photochemotherapy is generally used to treat and/or diagnose several types of ailments in or near the skin or other tissues, such as those in a body cavity. For example, PDT or PD may be used for treatment or diagnosis of actinic keratosis of the scalp or facial areas of a patient. In addition, PDT and PD may be used for treatment and diagnosis of other indications (e.g., acne, warts, psoriasis, photo-damaged skin, cancer) and other areas of the patient (e.g., arms, legs).

During one form of PDT or PD, a patient is first administered a photoactivatable agent or a precursor of a photoactivatable agent that accumulates in the tissue to be treated or diagnosed. The area in which the photoactivatable agent is administered is then exposed to visible light, which causes chemical and/or biological changes in the agent. These changes allow the agent to then selectively locate, destroy, or alter the target tissue while, at the same time, causing only mild and reversible damage to other tissues in the treatment area. One example of a precursor of a photoactivatable agent is 5-aminolevulinic acid ("ALA"), which is commonly used in PDT of actinic keratosis. As they are used here, the terms ALA or 5-aminolevulinic acid refer to ALA itself, precursors thereof and pharmaceutically acceptable salts of the same.

For effective treatment, it is desirable to have a power output that is uniform in intensity and color. Illuminators, such as those disclosed in U.S. Pat. Nos. 8,758,418; 8,216,289; 8,030,836; 7,723,910; 7,190,109; 6,709,446; 6,223,071, which are incorporated by reference in their entireties for the techniques, methods, compositions, and devices related to PDT and PD, are typically used to provide the proper uniformity of light for treatment purposes. These devices generally include a light source (e.g., a fluorescent tube), coupling elements that direct, filter or otherwise conduct emitted light so that it arrives at its intended target in a usable form, and a control system that starts and stops the production of light when necessary.

SUMMARY

Because PDT can be used to treat a variety of treatment areas, some illuminators utilize two or more panels, each panel having a light source to emit light at the intended target area. These panels are coupled together so as to be rotatable relative to each other. By incorporating multiple, rotatable panels, the overall size and shape of the area that is illuminated can be changed according to the intended treatment area.

In conventional adjustable illuminators, the panels are equally sized by width and length and are typically driven at the same power level. The panels are further joined at their edges by hinges so as to be rotatable to achieve a desired configuration. However, due to the edges of the panels and the presence of the hinges, the light source(s) of one panel does not immediately adjoin the light source(s) of an adjacent panel. As a result, light is not emitted from a "gap" between the light sources. The lack of light emitting from such areas, together with the uniform supply of power to the panels, can cause optical "dead space" in certain portions of the target treatment area. These portions, in turn, receive less overall light, resulting in a lower dose of treatment in those portions. In some instances, the dose of treatment can be lowered by as much as a factor of five when compared with those areas receiving an optimal amount of light.

Generally, these conventional illuminators are used for phototherapy of acne, which typically does not require the administration of a photoactivatable agent for effective treatment. Thus, exposure to the light alone is generally sufficient treatment. Moreover, because multiple treatment sessions can be utilized to effectively treat the condition, uniformity of light across the target area during a given treatment is less of a concern in some situations. However, some forms of treatment involving PDT, such as the use of ALA to treat actinic keratosis, require specific and highly uniform intensity and color of light to achieve effectiveness. In these instances, successful PDT relies on the targeted delivery of both the correct quantity of the photoactivatable agent and the correct quantity (i.e., power and wavelength) of light to produce the desired photochemical reactions in the target cells. Thus, to achieve this, the light source must provide illumination to the target area and this illumination must be uniform with respect to both wavelength and power. The optical dead space that can occur at or near the hinges of conventional adjustable illuminators reduces the uniformity of the light along the treatment area, thereby reducing the effectiveness of PDT for these specific treatments. Moreover, these illuminators are also configured to adjust within a limited range, such that only a limited amount of surfaces on a patient's body may be treated, such as a patient's face and scalp. In addition, due to the various contours of a patient's body, the uniformity of light delivered by these conventional illuminators may vary substantially depending on the treatment area of the patient.

Therefore, it is an object of some embodiments of the present invention to reduce or eliminate these dead spaces and provide for a more uniform light distribution in an adjustable illuminator designed for PDT or PD of a variety of targeted areas. In addition, it is an object of some embodiments of the present invention to provide an infinitely adjustable illuminator that can effectively deliver a uniformity of light across various areas of a patient's body, such as a patient's extremities (e.g., arms and legs) or torso, in addition to a patient's face and scalp. Thus, a uniform light may be delivered to a targeted treatment area regardless of the shape and location of the contoured surface of the patient's body.

One embodiment of the present invention uses a plurality of panels, wherein at least one panel is of a different width than the other panels. This panel is positioned between two other panels and, in a way, acts as a "lighted hinge" to provide enough "fill-in" light to reduce or eliminate the optical dead spaces when the panels are bent into a certain configuration. Preferably, five panels in total are used to provide for an optimal increase in the total size of possible treatment areas. Two of the panels are preferably of a smaller width than the other three larger panels. These panels are positioned in an alternating manner such that each of the smaller-width panels is situated in between two of the three larger panels to allow for both adjustability and increased uniformity. Furthermore, to further reduce or eliminate optical dead spaces, the panels are preferably coupled together using nested hinges, thereby reducing the area in which no light source is present on the illuminator. In order to even further reduce or eliminate optical dead spaces, it is preferable that the light sources on each of the panels are individually configurable to provide specific power output to certain areas of the light sources on the panels to compensate for decreased uniformity. For example, the power outputted to each individual diode in an array of light emitting diodes (LED) may be individually adjusted.

BRIEF DESCRIPTION OF THE DRAWINGS

Features, aspects, and advantages of the present invention will become apparent from the following description and the accompanying exemplary embodiments shown in the drawings, which are briefly described below.

FIGS. 1A-1B show top views of a main body of an illuminator according to an exemplary embodiment.

DETAILED DESCRIPTION

Figure 2B:
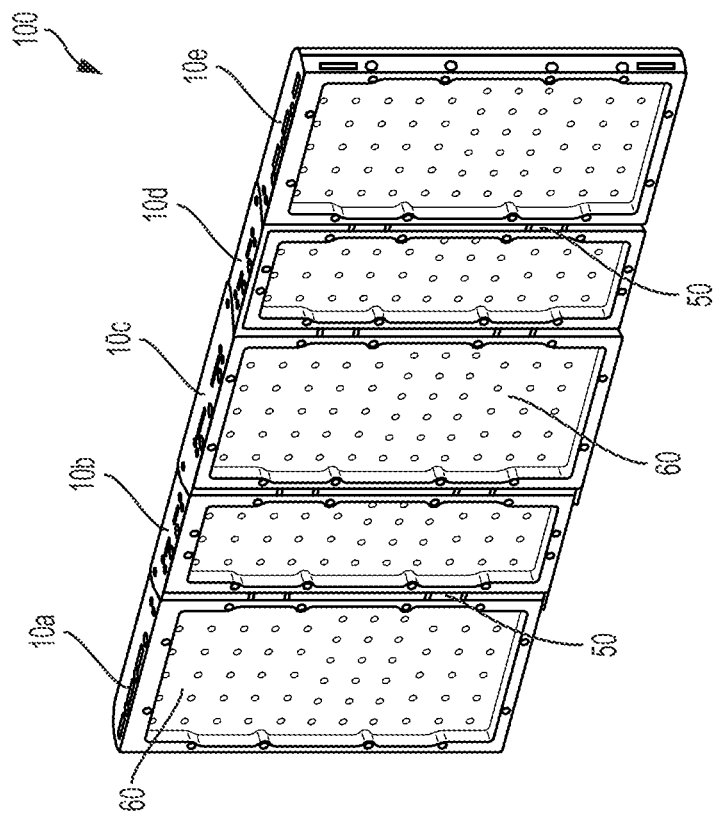
FIGS. 2A-2B show perspective views of the main body of the illuminator of FIGS. 1A-1B.

FIGS. 1A-1B and 2A-2B illustrate one embodiment of a configurable illuminator according to the present invention. The illuminator includes a main body 100, which preferably has five individual panels 10a-10e, each of which are connected in a rotatable manner via nested hinges 50. Each panel contains an array of light emitting diodes (LED) 60, which may be configured in an evenly spaced pattern across the face of the panel. The number of individual LEDs arranged in a given array is not particularly limited. Alternatively, other types of light sources may be used, such as fluorescent or halogen lamps.

Preferably, each LED array 60 extends as far to the edges as possible. In addition, the LED arrays 60 are preferably dimensioned to provide an overall lighted area for a given treatment area based on a range from the 5th percentile of corresponding female sizes to the 95th percentile of corresponding male sizes for that particular treatment area. The LED arrays 60 emit light at an appropriate wavelength according to the intended treatment or to activate the particular photoactivatable agent used in treatment or diagnosis. For example, when ALA is used as a precursor of a photoactivatable agent for the treatment of actinic keratosis, the LED arrays 60 preferably emit blue light having wavelengths at or above 400 nanometers (nm), for example, about 430 nm, about 420 nm or, for example, 417 nm. However, the LED arrays 60 may also emit visible light in other ranges of the spectrum, such as in the green and/or red ranges between 400 and 700 nm, for example, about 625 nm to 640 nm or, for example, 635 nm. For example, the LED arrays 60 may also emit light having wavelengths of 510 nm, 540 nm, 575 nm, 630 nm, or 635 nm. In addition, the LED arrays 60 may be configured to emit light continuously or the LED arrays 60 may be configured to flash the diodes on and off based on a predetermined interval. Furthermore, the LED arrays 60 may be configured such that only one wavelength of light (e.g., blue) is emitted. Alternatively, the LED arrays 60 may be configured such that two or more wavelengths of light are emitted from the arrays. For example, the LED arrays 60 may be configured to alternately emit blue light and red light for treatment purposes.

Figure 6:
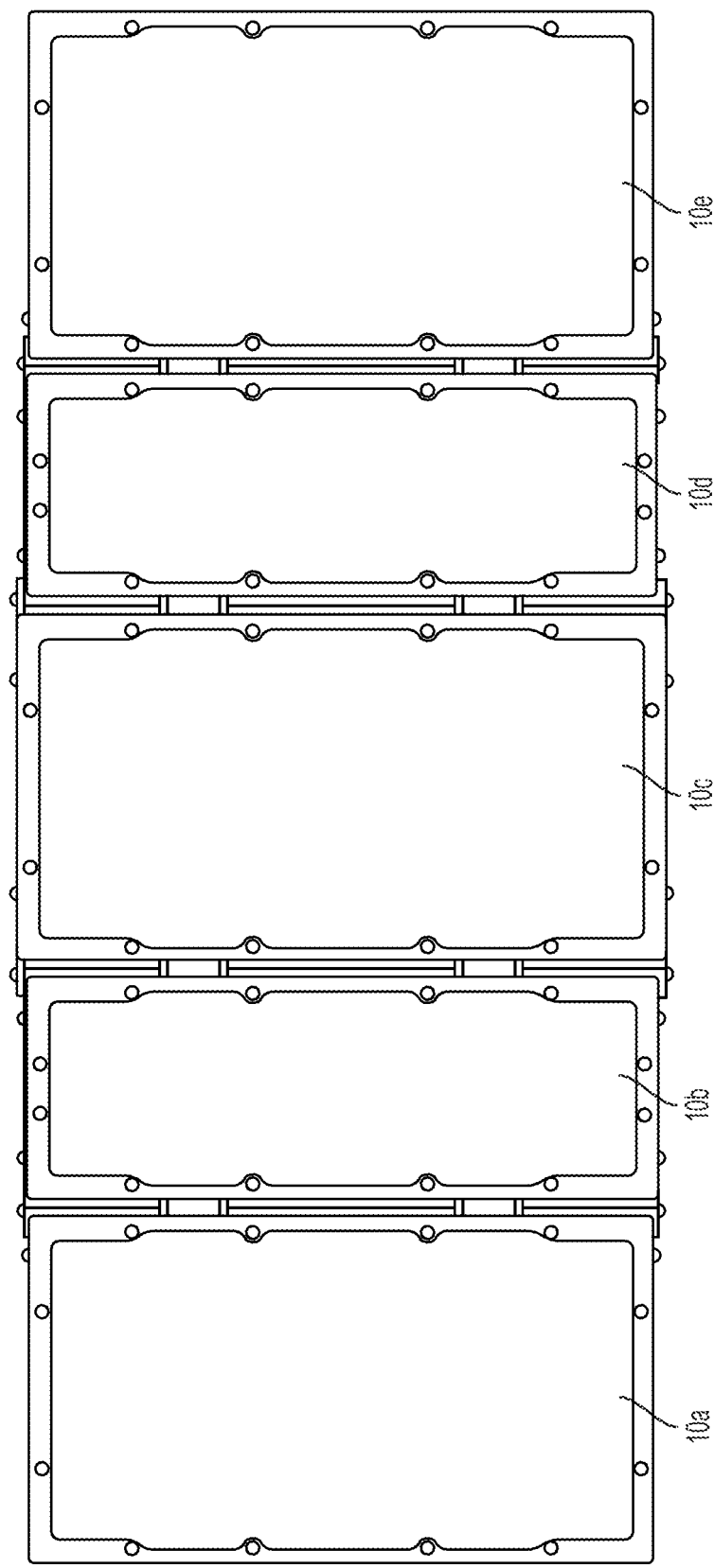
FIG. 6 shows a schematic view illustrating widths and lengths of individual panels of the main body of the illuminator of FIGS. 1A-1B.

As shown in FIGS. 1A-1B and 2A-2B, the five panels 10a-10e are of different widths relative to one another. In particular, in certain embodiments, three panels 10a, 10c, 10e are configured to have wider widths, while two panels 10b, 10d have smaller, narrower widths, each of the narrower widths of the two panels 10b, 10d being less than each of the wider widths of the three panels 10a, 10c, 10e. In some embodiments, the wider widths of the three larger panels 10a, 10c, 10e are approximately equal. In other embodiments, the wider widths of the three larger panels 10a, 10c, 10e are different relative to one another. In addition, the narrower widths of the two panels 10b, 10d may be approximately equal or may be different relative to one another. The panels are further arranged in an alternating configuration, with the narrower panels (e.g., 10b) positioned in between two wider panels (e.g., 10a, 10c). As shown in FIG. 6, in some embodiments, the narrower panels 10b, 10d are configured to have a width that is about 30% to 60% less than the width of the wider panels 10a, 10c, 10e. In other embodiments, the narrower panels 10b, 10d are configured to have a width that is about 30% to 50% less than the width of the wider panels 10a, 10c, 10e.

Figure 2A:
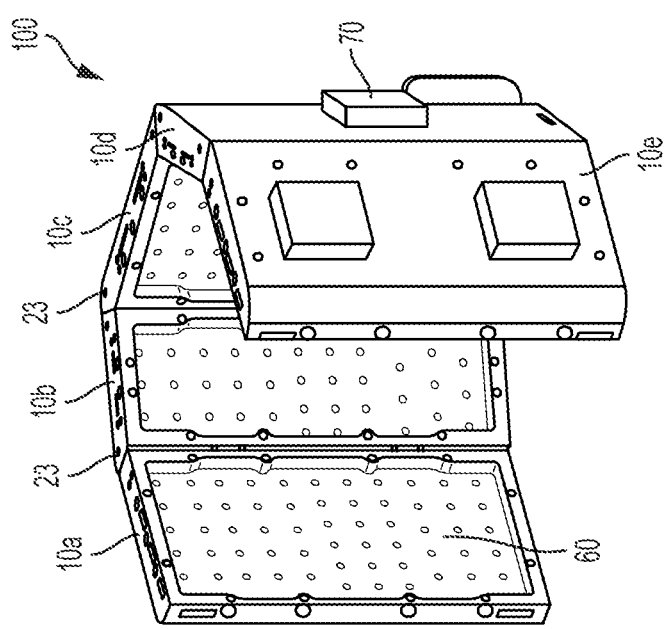

As shown in FIGS. 1A-1B and 2A-2B, the panels 10a-10e are rotatably connected by hinges 50. The hinges 50 may take the form of nested hinges, which may include hinges that substantially reduce or eliminate optical dead spaces. As shown in FIGS. 2A-2B, on at least one side of a panel, a tab 23 may extend out from both the top and bottom of the panel. The tabs 23 are configured such that a side of an adjacent panel may be received between the tabs 23, as shown in FIG. 2A. Thus, as best seen in FIGS. 2A-2B and 6, the height of the adjacent panel (e.g., panel 10a) is slightly smaller than the height of the tabbed panel (e.g., panel 10b) into which the adjacent panel is received. As shown in FIG. 6, the middle panel (i.e., panel 10c) is preferably configured as having the largest height, such that it is tabbed on both sides and may receive the sides of adjacent panels on each side. As seen in FIGS. 1A-1B, each of the tabs 23 further includes an opening to receive a bolt to connect adjacent panels together.

Figure 3A:
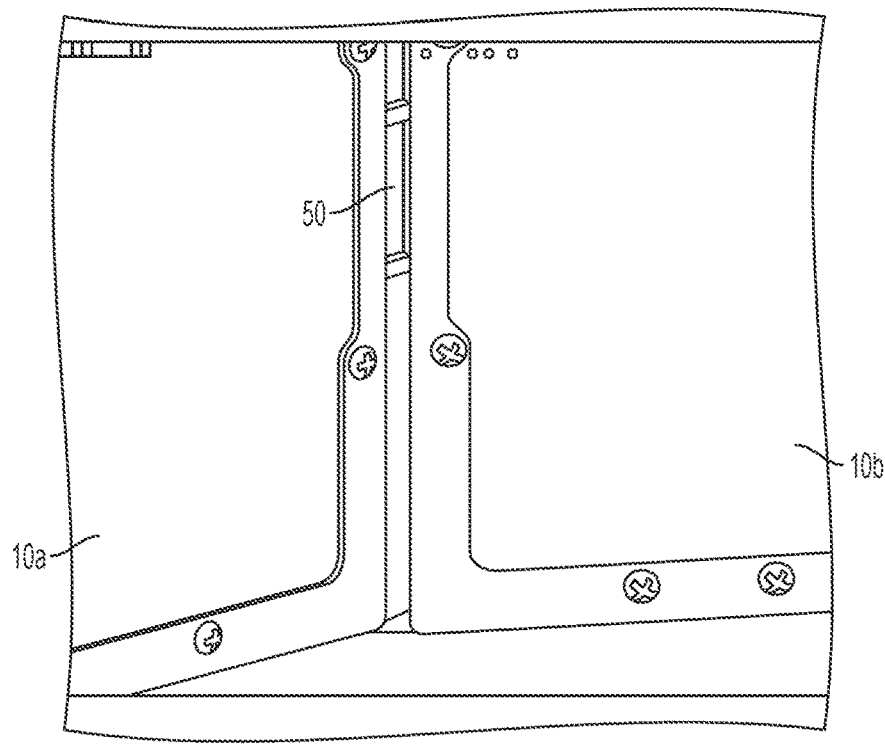
FIGS. 3A-3B show detailed views of the nested hinges of the main body of the illuminator of FIGS. 1A-1B.
Figure 3B:
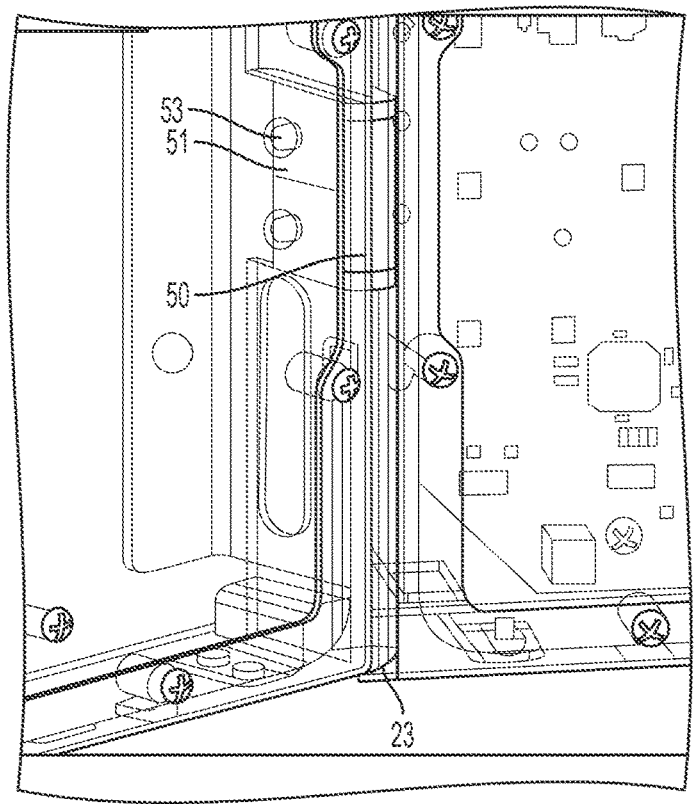

As shown in further detail in FIGS. 3A-3B, between the tabs 23 are the nested hinges 50, which are mounted to the inner side surfaces of adjacent panels (e.g., 10a, 10b) to allow for rotation of the panels. A flange 51 of the hinge 50 is mounted to the inner side surface of a panel via bolts 53. The inner side surface of a panel may include a recess in which the flange 51 may be placed. The inner side surface of the panel may also include an additional recess to accommodate the joint of the hinge 50 such that the joint of the hinge 50 becomes substantially flush with an outer front surface of the panel. Such configurations may allow for the outside vertical edges of adjoining panels to be positioned closer to one another. By spacing the vertical edges of adjoining panels closer, optical dead spaces may be further reduced or eliminated. In addition, the hinges 50 together with the tabs 23 may reduce the number of pinch points present in the system.

Figure 4:
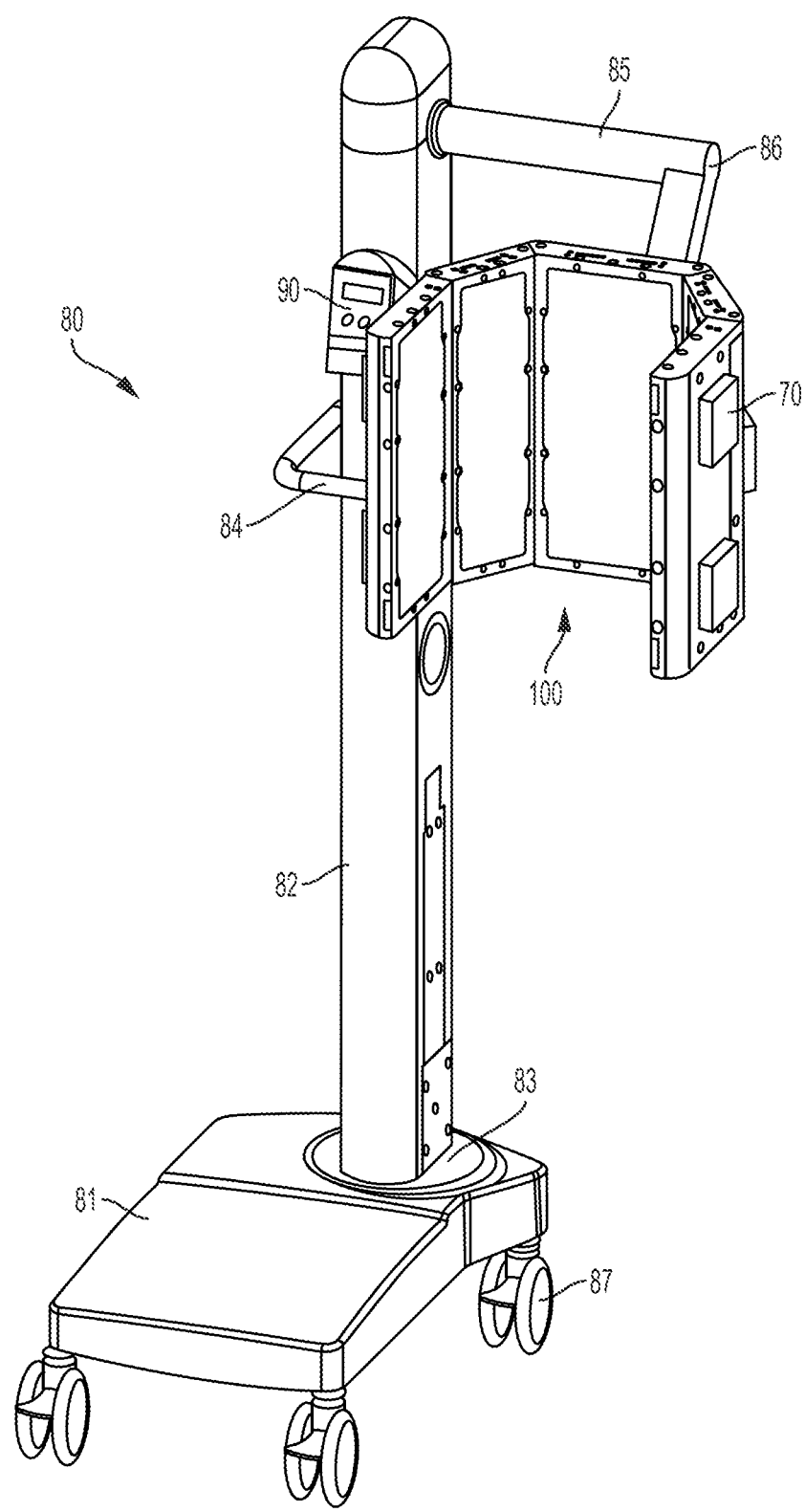
FIG. 4 shows a perspective view of the illuminator having the main body of FIGS. 1A-1B mounted to a stand.

As shown in FIGS. 1A-1B, the main body 100 of the illuminator may include a mounting head 40. The mounting head 40 may allow for the main body 100 to be mounted to a movable stand 80, which is shown in FIG. 4, to allow a user to easily move the main body 100 to the appropriate treatment position. The stand 80 includes a base 81 and a vertical pillar 82. The base 81 may further include wheels 87 at its bottom in order to allow the user to horizontally move the illuminator to an appropriate position. The wheels 87 may include locks, such that the stand 80 is prevented from further horizontal movement once positioned. In addition, the vertical pillar 82 may be attached to the base 81 at a pivot point 83. The pivot point 83 allows the vertical pillar 82 to be rotated to increase the range of positioning for the illuminator. At a top end, the vertical pillar 82 includes a connecting arm 85, which may serve as a mounting structure for the main body 100. The connecting arm 85 includes a hinge point 86 such that the main body 100 can be moved vertically relative to the stand 80. The vertical pillar 82 may also be configured as a telescopic structure, such that the user can change the height of the vertical pillar 82. This allows for an increased range of vertical movement for the main body 100, which can allow the user to position the main body 100 at lower portions of a treatment area, such as a patient's legs or feet. The stand 80 may also include a stabilization arm 84. Once the stand 80 and main body 100 is positioned, the stabilization arm 84 may be attached to the main body 100 to prevent unwanted movement of the main body 100 during treatment. As further shown in FIG. 4, a controller and power supply 90 is mounted to the stand 80 in order to supply electrical power to the main body 100 and allow the user to control the main body 100 for treatment purposes. Alternatively, the controller and power supply 90 may be directly mounted to the main body 100. In order to provide a cooling system for the LED arrays 60, one or more fans 70 may be mounted onto each of the panels, as shown in FIG. 4.

At least one control unit is also connected to the panels to regulate power to the lights to achieve the required uniformity and intensity for the target treatment. The control unit may be implemented as hardware, software, or a combination of both, such as a memory device storing a computer program and a processor to execute the program. Alternatively, each panel may have a dedicated control unit to regulate power to the individual LED array on a given panel to allow for more particular fine-tuning of the illuminator, which may further enhance uniformity and increase efficiency. For example, under Lambert's cosine law, light intensity at a given point on a "Lambertian" surface (such as skin) is directly proportional to the cosine of the angle between the incoming ray of light and the normal to the surface. Thus, a ray of light that is directed to the front of a curved surface (e.g., a head of a patient) will arrive in a substantially perpendicular manner to that area and will result in 100% absorbance. However, a ray of light that arrives at a side edge of the curved surface will arrive in a substantially parallel manner. According to Lambert's cosine law, the intensity, and thus absorption, of the light at the side edge will approach zero, making treatment at that area ineffective. Thus, a "fall off" of light exposure tends to occur at the edges of a curved surface. In addition, "fall off" increases as the distance between the light source and the point on the surface increases.

Configuring an illuminator to conform to the curved surface (e.g., a U-shaped configuration designed to "wrap around" the curvature of the surface) aids in reducing this effect and increases overall uniformity. However, to sufficiently increase uniformity, the light source should be larger relative to the target treatment area in order to fully encompass the body part to be treated and also provide light from all angles to any target point on the treatment area. In order to increase the uniformity of light exposure to the treatment area while maintaining a practical size of the illuminator, the LED arrays 60 may be individually configured to increase the intensity of light emitting from certain diodes to compensate for this fall-off effect.

Figure 5:
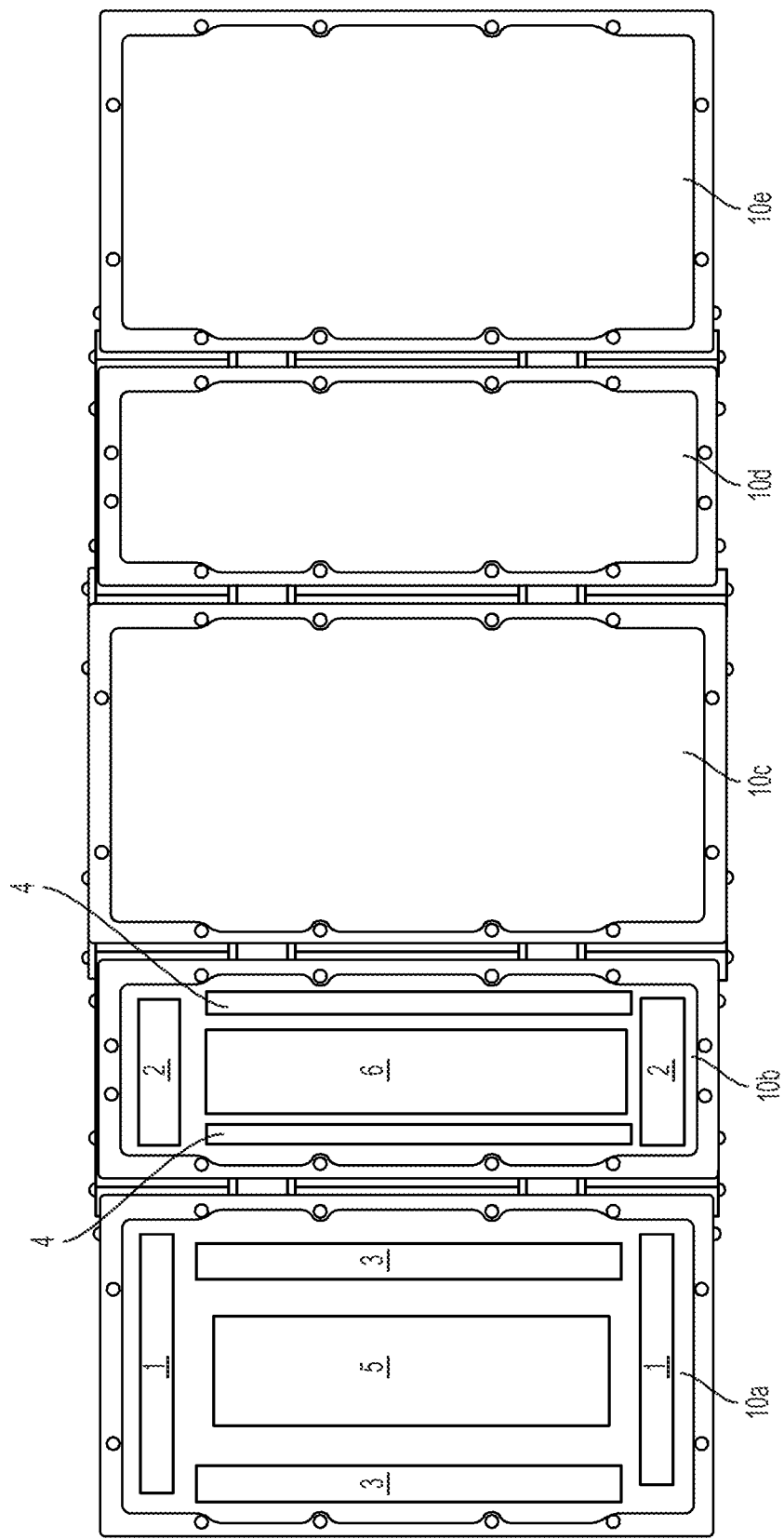
FIG. 5 shows a schematic view illustrating an addressable configuration of LEDs mounted on the main body of the illuminator of FIGS. 1A-1B.

An example in which the LED arrays 60 may be individually configured is shown in FIG. 5. Here, the LED arrays 60 are divided into three general areas, which may be described as "addressable strings." Areas 1, 3, and 5 correspond to an addressable string configuration that may be included in the wider panels 10a, 10c, and 10e, while areas 2, 4, and 6 correspond to an addressable string configuration that may be included in the narrower panels 10b and 10d. The current to each area is adjusted in order to adjust the intensity of light emitting from each of the areas. For example, a higher current may be supplied to areas 1 and 2 than the current supplied to areas 3 and 4 such that areas 1 and 2 emit a higher intensity of light than areas 3 and 4. Similarly, a higher current may be supplied to areas 3 and 4 than the current supplied to areas 5 and 6. Thus, a higher intensity of light is emitted overall from the edges, which may allow for a reduction in any fall-off effect. Alternatively, the illuminator may be configured to adjust each individual diode present in a given LED array 60, allowing for an even greater fine-tuning effect. Furthermore, by using either pre-programmed settings or sensors to detect the curvature of the surface to be treated, the LED arrays 60 can be individually configured to emit more intense light to only those areas that require it. This allows for an increase in uniformity of light exposure in an efficient manner as power output and/or light intensity is increased to only certain diodes, in accordance with need.

The addressable strings of the LED arrays 60 may also include varying amounts of individual diodes mounted within the particular area. For example, for the wider panels 10a, 10c, and 10e, 12 diodes may be mounted in each of areas 1, while 9 diodes may be mounted in each of areas 3 and 41 diodes may be mounted in area 5, resulting in a total of 83 individual diodes included within each of the wider panels 10a, 10c, and 10e. For the narrower panels 10b and 10d, 8 diodes may be mounted in each of areas 2, while 9 diodes may be mounted in each of areas 4, and 23 diodes may be mounted in area 6, resulting in a total of 57 individual diodes included within each of the narrower panels 10b and 10d. However, the number and arrangement of diodes included within each of the LED arrays 60 is not particularly limited. For example, the wider panels 10a, 10c, and 10e may each contain a total amount of diodes that ranges from about 80 diodes to about 350 diodes. Similarly, the narrower panels 10b and 10d may each contain a total amount of diodes that ranges from about 50 diodes to about 250 diodes. By varying the arrangement of the diodes within each of the addressable strings of the LED arrays 60, power output and/or the intensity of light emitted from a given array may be better controlled and fine-tuned.

In addition, individually regulating power to the LED arrays 60 can also contribute to the reduction or elimination of the optical dead spaces that may otherwise occur at the hinge points. Specifically, power output and/or the emitted light intensity may be increased close to the edges of the array that are closest to the nested hinges to compensate for the lack of light emitting from the meeting point of panels. The narrower panels 10b, 10d are also preferably operated at a higher power level and/or at a higher emitted light intensity compared to the wider panels 10a, 10c, 10e in order to provide additional fill-in light. Furthermore, individual power regulation may aid in compensating for manufacturing variance that can occur in individual diodes. Finally, by fine-tuning each array 60, the panels can be easily deployed for other applications as each array is specifically configurable to address the lighting needs of the specific application.

The illuminator may further include a timer, which can indicate to the user the appropriate length of exposure time for the particular treatment. The illuminator may also be programmed with pre-stored light dosing parameters to allow the user to select a desired treatment type. The pre-stored parameters may include, for example, pre-stored settings for exposure time, light intensity, and outputted wavelength. Based on the selected treatment, the illuminator is automatically configured to provide the correct lighting dosage by being supplied with the appropriate power output to achieve the required uniformity for the treatment. Alternatively, the illuminator can be provided with sensors that detect the size of the treatment area positioned in front of the illuminator. The sensors then determine the correct light dosing parameters based on the sensed treatment area. The illuminator may also further include actuators and may be programmed to be moved automatically depending on the selected treatment. Once a treatment is selected, the illuminator may be automatically positioned into the proper configuration by the actuators without requiring the user to move the system by hand. Alternatively, the sensors may detect the adjusted position of the illuminator manually set by the user. The detected position of the illuminator may then be used to indicate the intended treatment area. Correct light dosing parameters for the specific treatment area may then be provided based on the detected position set by the user.

The adjustable illuminator of the present invention allows for an infinite amount of configurations that can be adapted for the targeted treatment area. The configurations may range from a flat-plane emitter (as shown in FIGS. 1B and 2B) to a substantially U-shaped configuration (as shown in FIGS. 1A and 2A). The adjustable illuminator may also be configured such that the two end panels 10a, 10e can be pulled back relative to the three middle panels 10b, 10c, 10d, such that a smaller U-shaped configuration may be created by the middle panels. Thus, the adjustable illuminator allows for the treatment of additional areas of a patient's body. In other words, not only can the adjustable illuminator effectively deliver a uniform light intensity to traditional surfaces such as the face or scalp, but the adjustable illuminator can also provide a device that can easily be configured to treat other portions of a patient's body, in particular, those having smaller curved surfaces, such as the arms and legs. Moreover, the adjustable illuminator may also be easily positioned to deliver a uniform light intensity to larger treatment areas, such as the back or chest.

Figure 7:
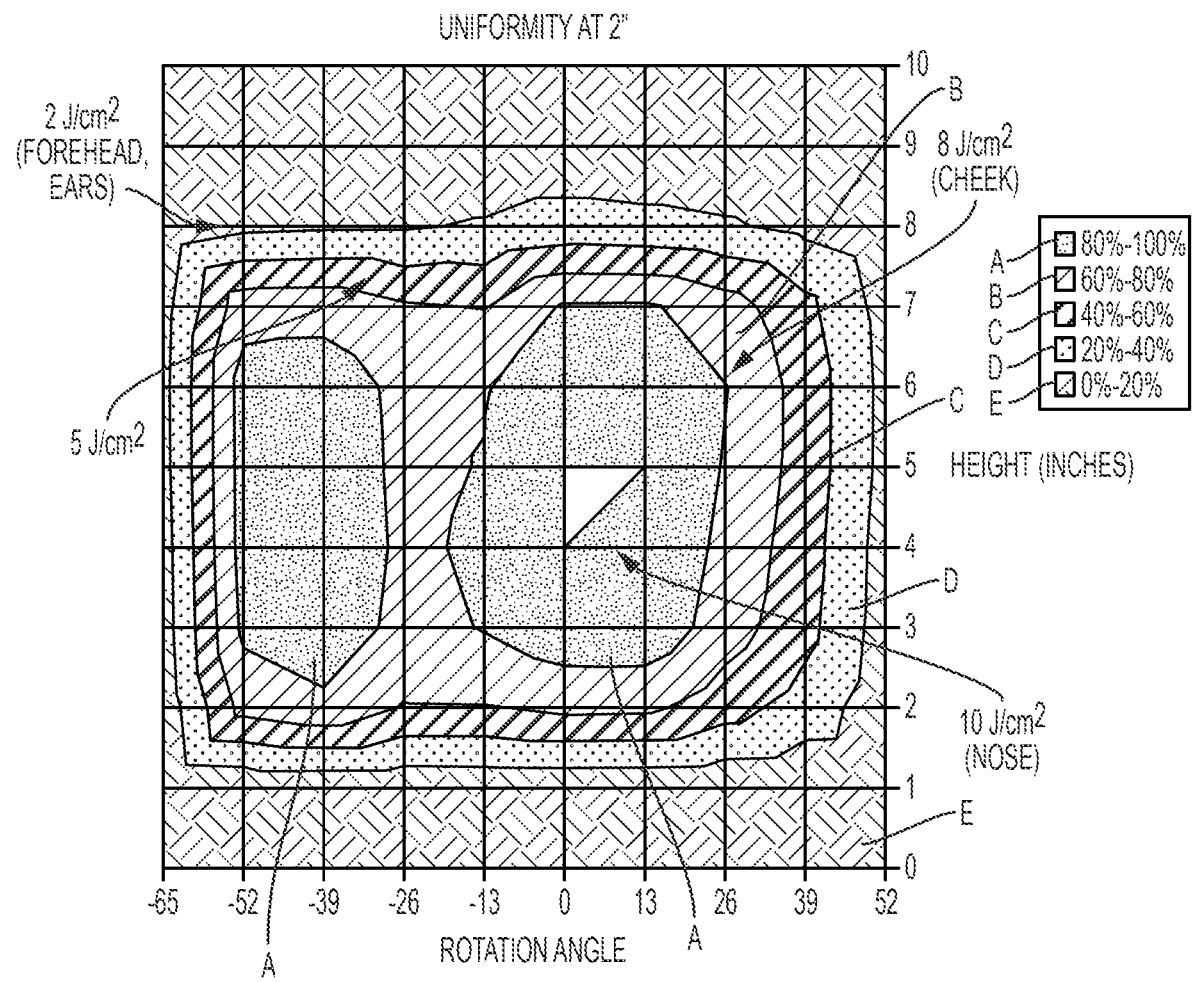
FIG. 7 shows a graph illustrating light dosage across a treatment area according to a conventional paneled illuminator.

As described above, the narrower panels 10b, 10d are dimensioned such that the panels act as "lighted hinges." Thus, when the wider panels 10a, 10c, 10e are adjusted into the desired form, the illuminator "bends" at the narrower panels 10b, 10d, where traditionally the "bend" would occur substantially at the hinge itself. Thus, instead of an unlighted "bent" portion as would occur in the conventional illuminator, the present illuminator provides a "bent" portion that is also configured to emit light, thereby helping to reduce optical dead space without requiring large amounts of power differentiation among the light sources of each panel to provide the required fill-in light. The effects of this configuration can be best seen in a comparison of FIGS. 7 and 8. FIG. 7 illustrates the light uniformity produced by a conventional illuminator, measured with a cosine response detector, which mimics the response of a patient's skin to the incident of light as described above, at a distance of two inches. Total light dose, in terms of $J/cm^2$, was measured based on emitted irradiance ($W/cm^2$) over time (in seconds). The targeted treatment area shown is a patient's head, where height is shown as the y-axis and rotation angle from the center of the emitting surface is shown as the x-axis. As can be seen in FIG. 7, higher light doses of about 10 $J/cm^2$ occur at the center of the face (for example, at region A), near the patient's nose, where the patient is facing closest to, and substantially perpendicular to, the middle-most panel. Total light dose then begins to drop as movement away from the center of the face occurs where the effects of cosine "fall-off" and optical dead spaces are more prevalent. For example, light dose is reduced by about 20% at the patient's cheek areas (for example, at region B), and by about 80% toward the outer boundaries of the patient's face (for example, at region E), such as the ears and forehead. Thus, as shown in FIG. 7, conventional adjustable illuminators utilizing equally-sized panels operating at the same power output level produce a varying field of light uniformity, making it undesirable and ineffective for those treatments requiring highly specific light uniformity.

Figure 8:
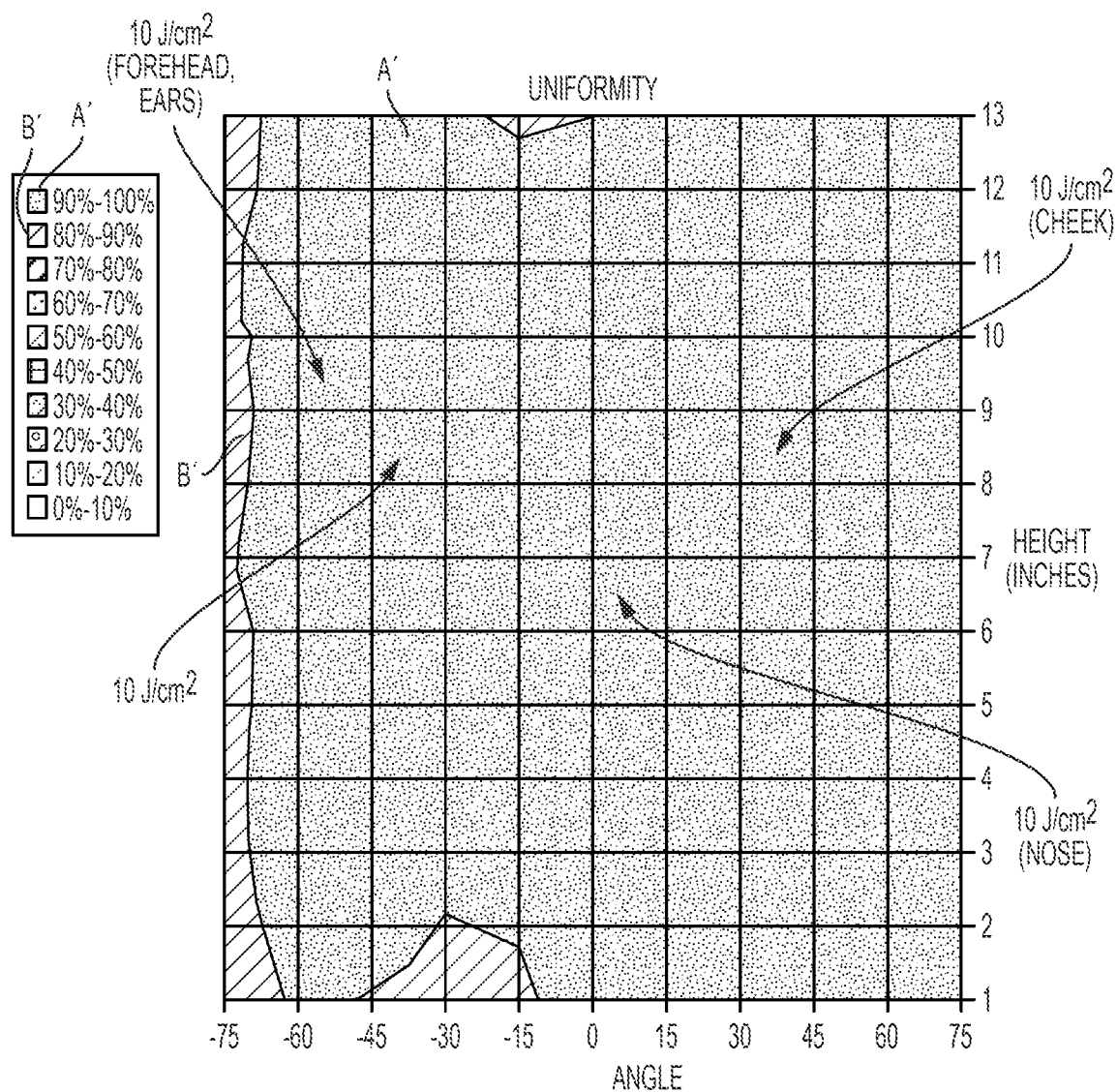
FIG. 8 shows a graph illustrating light dosage across the same treatment area as FIG. 7 using an illuminator according to one embodiment of the present invention.

FIG. 8, on the other hand, illustrates the light uniformity produced by an embodiment of the present invention. The targeted treatment area is the same as that measured in FIG. 7. However, compared to FIG. 7, the light output uniformity produced by the illuminator is greatly enhanced across the patient's face and exhibits little to no deviation from the light output measured in the center of the patient's face to the light output measured at the edges of the patient's face. For example, as shown in FIG. 8, total light doses of about 10 $J/cm^2$ (for example, at region A') occur across all regions of the face, including the center of the face (for example, the patient's nose), the patient's check areas, and the outer boundaries of the patient's cheek areas, such as the ears and forehead. Moreover, total light dose drops off minimally (for example, at region B') at the extreme outer boundaries of the patient's face. In one embodiment, the measured output over the active emitting area (over the entire active emitting area) is within 60% of the measured maximum (over the entire active emitting area) measured with a cosine response detector over all operation distances. More preferably, the measured output over the emitting area is within 70% of the measured maximum over a distance of two and four inches. Even more preferably, the measured output over the emitting area is within 80% of the measured maximum over a distance of two and four inches.

One example of a treatment method for precancerous lesions, such as actinic keratosis, by PDT utilizing an adjustable illuminator described above in conjunction with ALA will now be described.

Essentially anhydrous ALA is admixed with a liquid diluent just prior to its use. The ALA admixture is topically applied to the lesions using a point applicator to control dispersion of the ALA admixture. After the initial application of the ALA admixture has dried, one or more subsequent applications may be similarly applied. Approximately 2 mg/cm$^2$ of ALA is administered. Formation of photosensitive porphyrin and photosensitization of the treated lesions occurs over the next 14-18 hours, during which time exposure to direct sunlight or other bright light sources should be minimized. Between 14 and 18 hours after administration of the ALA, the lesions are irradiated by the adjustable illuminator according to the present invention. The illuminator irradiates the lesions with a uniform blue light for a prescribed period. According to a preferred treatment, the visible light has a nominal wavelength of 417 nm. The illuminator may irradiate the lesions with a uniform red light for a prescribed period. In certain embodiments, the illuminator irradiates the lesions with a uniform blue light for a first prescribed period and then irradiates the lesions with a uniform red light for a second prescribed period. For example, in some embodiments, the illuminator is configured to irradiate the lesions with a uniform blue light (e.g., 417 nm) at a low intensity (e.g., about 0.1 J/cm$^2$ to about 2 J/cm$^2$) to photobleach, for example, protoporphyrin IX (PpIX) present at the surface of the patient's skin, and irradiate the lesions with a uniform red light (e.g., 635 nm) at a high intensity (e.g., about 30 J/cm$^2$ to about 150 J/cm$^2$) to activate PpIX present at deeper layers of the patient's skin, thus avoiding potential damage to the upper layers of the patient's skin. The illuminator may be configured to simultaneously irradiate the patient's skin with the low intensity blue light and the high intensity red light or sequentially irradiate the patient's skin with the low intensity blue light and the high intensity red light. In certain embodiments, the illuminator is configured to irradiate the patient's skin with the low intensity blue light for about one hour to about three hours and irradiate the patient's skin with the high intensity red light for about 20 minutes to about 30 or 40 minutes, either at the same time the patient's skin is irradiated with the low intensity blue light or after the patient's skin has been irradiated with the low intensity blue light.

The invention thus provides a method for photodynamically diagnosing or treating a contoured surface of a patient, which includes providing the adjustable illuminator described above, placing the patient in the illuminator, and illuminating the patient to diagnose or treat the patient. The patient may be illuminated to treat actinic keratosis, acne, photo-damaged skin, cancer, warts, psoriasis, or other dermatological conditions. The method may also be used to remove hair and diagnose cancer.

Since the total light dose (J/cm$^2$) is equal to irradiance (W/cm$^2$) multiplied by time (sec), the only additional parameter that needs to be controlled for delivery of the correct treatment light dose is exposure time. This may be accomplished by the timer described above, which can control the electrical power supplied to the LED arrays 60 appropriately, and which can be set by the physician. Data has shown that 10 J/cm$^2$ delivered from a source with an irradiance density of 10 mW/cm$^2$, or an irradiance density of about 9.3 to about 10.7 mW/cm$^2$, produces clinically acceptable results for desired treatment areas (e.g., face, scalp, extremities). From the equation above, this light dose will require an exposure time of 1000 seconds (16 min. 40 sec). In addition, due to the addressable nature of the adjustable illuminator, the illuminator may be used to treat a patient at higher power such that less time is required for effective treatment. For example, the adjustable illuminator may deliver an irradiance density of 20 mW/cm$^2$ for an exposure time of 500 seconds (8 min. 20 sec) to deliver a clinically acceptable light dose of 10 J/cm$^2$. Alternatively, the adjustable illuminator may include higher power ranges, such as 30 mW/cm$^2$, over an exposure time resulting in a light dose of 10 J/cm$^2$. A selected light dose may also be administered by additionally or alternatively varying the irradiance density over treatment time.

Additional advantages and modifications will readily occur to those skilled in the art. Therefore, the invention in its broader aspects is not limited to the specific details and representative devices and methods, shown and described herein. Accordingly, various modifications may be made without departing from the spirit and scope of the general inventive concept as defined by the appended claims and their equivalents.

What is claimed is:

1. A method of photodynamically diagnosing or treating a patient, the method comprising:
   applying 5-aminolevulinic acid (ALA) to a treatment surface on an extremity of the patient,
   illuminating, by an illuminator comprising a plurality of light sources disposed on surfaces of a plurality of panels, the treatment surface of the patient;
   wherein the plurality of panels are connected by hinged structures on inner side surfaces of adjacent panels, wherein the illuminator is configured to uniformly illuminate the treatment surface via the light sources;
   positioning one of the plurality of panels as a center panel to face the treatment surface; and
   positioning two or more of the plurality of panels to be extended from the center panel such that the plurality of panels are positioned to allow treatment of the extremities of the patient;
   wherein each of the plurality of panels has two first edges and two second edges shorter than the two first edges, and the light sources are arranged such that a higher intensity of light is emitted proximate the second edges compared to the intensity of light emitted not proximate the second edges.

2. The method of claim 1, wherein illuminating comprises outputting red light at a dose of about 30 J/cm$^2$ to about 150 J/cm$^2$.

3. The method of claim 1, wherein illuminating comprises outputting light at a variable irradiance density during treatment.

4. The method of claim 1, wherein illuminating comprises outputting light at an irradiance density of 10 mW/cm$^2$ to 30 mW/cm$^2$.

5. The method of claim 1, wherein a plurality of the light sources are configured to emit light having a wavelength in a range of 400 nm to 700 nm.

6. The method of claim 1, wherein illuminating comprises controlling illumination from each of the plurality of panels.

7. The method of claim 1, wherein the treatment surface is located on the arms, legs or feet.

8. The method of claim 1, wherein about 2 mg/cm$^2$ of ALA is applied to the treatment surface.

9. A system for photodynamically diagnosing or treating a patient, comprising:

an illuminator comprising five panels connected by hinged structures on inner side surfaces of adjacent panels;

light sources disposed on the five panels of the illuminator, the light sources being configured to uniformly illuminate a treatment surface of the patient, and a controller and at least one sensor, the controller being configured to change intensities of the light sources of the illuminator with a controller in accordance with information received from the at least one sensor relating to a curvature of the treatment surface, wherein each of the five panels has two first edges and two second edges shorter than the two first edges, and the light sources are arranged such that a higher intensity of light is emitted proximate the second edges compared to the intensity of light emitted not proximate the second edges, wherein each of the five panels is configured to allow selective control of illumination therefrom.

10. The system of claim 9, wherein the light sources are configured to illuminate the treatment surface by outputting red light during at least part of the time when the treatment surface is illuminated.

11. The system of claim 9, wherein the light sources are configured to illuminate the treatment surface by outputting blue light during at least part of the time when the treatment surface is illuminated.

12. The system of claim 9, wherein:

the illuminator comprises at least three first panels having first widths, at least two second panels having second widths, wherein each of the second widths of the at least two second panels is narrower than each of the first widths of the at least three first panels; and the at least three first panels and the at least two second panels are connected in an alternating manner such that each of the at least two second panels has a first lateral side connected to a respective one of the at least three first panels and a second lateral side connected to another respective one of the at least three first panels.

13. The system of claim 9, wherein the sensor is configured to determine a size of the treatment surface of the patient.

14. The system of claim 13, wherein the controller is configured to adjust an overall light dose based on the determined size of the treatment surface.

15. The system of claim 13, further comprising at least one actuator configured to adjust positioning of panels based on the determined size of the treatment surface.

\* \* \* \* \*